(12) United States Patent
Manuilov et al.

(10) Patent No.: US 9,170,262 B2
(45) Date of Patent: Oct. 27, 2015

(54) COMPARISON OF PROTEIN SAMPLES

(75) Inventors: Anton V. Manuilov, Burlington, MA (US); David H. Lee, Arlington, MA (US)

(73) Assignee: AbbVie, Inc., Chicago, IL (US)

( * ) Notice: Subject to any disclaimer, the term of this patent is extended or adjusted under 35 U.S.C. 154(b) by 886 days.

(21) Appl. No.: 13/161,907

(22) Filed: Jun. 16, 2011

(65) Prior Publication Data

US 2011/0312010 A1  Dec. 22, 2011

Related U.S. Application Data

(60) Provisional application No. 61/355,269, filed on Jun. 16, 2010.

(51) Int. Cl.
G01N 33/68 (2006.01)

(52) U.S. Cl.
CPC .................................. *G01N 33/6848* (2013.01)

(58) Field of Classification Search
None
See application file for complete search history.

(56) References Cited

U.S. PATENT DOCUMENTS

| | | | |
|---|---|---|---|
| RE30,985 E | 6/1982 | Cartaya | |
| 4,399,216 A | 8/1983 | Axel et al. | |
| 4,510,245 A | 4/1985 | Cousens et al. | |
| 4,560,655 A | 12/1985 | Baker | |
| 4,634,665 A | 1/1987 | Axel et al. | |
| 4,657,866 A | 4/1987 | Kumar | |
| 4,767,704 A | 8/1988 | Cleveland et al. | |
| 4,816,397 A | 3/1989 | Boss et al. | |
| 4,816,567 A | 3/1989 | Cabilly et al. | |
| 4,927,762 A | 5/1990 | Darfler | |
| 4,968,615 A | 11/1990 | Schaffner et al. | |
| 5,122,469 A | 6/1992 | Mather et al. | |
| 5,168,062 A | 12/1992 | Stinski | |
| 5,179,017 A | 1/1993 | Axel et al. | |
| 5,223,409 A | 6/1993 | Ladner et al. | |
| 5,225,539 A | 7/1993 | Winter | |
| 5,476,996 A | 12/1995 | Wilson et al. | |
| 5,530,101 A | 6/1996 | Queen et al. | |
| 5,585,089 A | 12/1996 | Queen et al. | |
| 5,693,762 A | 12/1997 | Queen et al. | |
| 5,698,767 A | 12/1997 | Wilson et al. | |
| 6,180,370 B1 | 1/2001 | Queen et al. | |
| 6,914,128 B1 | 7/2005 | Salfeld et al. | |

(Continued)

FOREIGN PATENT DOCUMENTS

| | | |
|---|---|---|
| EP | 1 420 254 | 5/2004 |
| EP | 1 686 372 | 8/2006 |

(Continued)

OTHER PUBLICATIONS

Ong, S. E., et al., 2003, "Mass spectrometric-based approaches in quantitative proteomics", Methods, vol. 29, pp. 124-130.*

(Continued)

*Primary Examiner* — Manjunath Rao
*Assistant Examiner* — William W Moore
(74) *Attorney, Agent, or Firm* — Lathrop & Gage, LLP; Andrew T. Wilkins

(57) ABSTRACT

Methods of qualitatively and/or quantitatively detecting the presence of mutations, modifications or impurities in a protein sample are provided. The methods utilize isotopically labeled variants of amino acids incorporated into proteins prior to protein digest to enable comparisons of two protein samples in bottom-up liquid chromatography.

17 Claims, 20 Drawing Sheets

(56) References Cited

U.S. PATENT DOCUMENTS

| | | | |
|---|---|---|---|
| 2006/0134723 | A1 | 6/2006 | Fischer et al. |
| 2007/0154900 | A1 | 7/2007 | Schneider et al. |
| 2008/0057592 | A1 | 3/2008 | Oda |
| 2008/0058246 | A1* | 3/2008 | Bhaskaran et al. ............... 514/2 |
| 2008/0299595 | A1 | 12/2008 | Wong et al. |
| 2009/0011447 | A1* | 1/2009 | Banoub et al. ................... 435/13 |
| 2009/0181004 | A1* | 7/2009 | Kaariainen et al. .......... 424/94.6 |
| 2010/0143912 | A1 | 6/2010 | Wells et al. |
| 2010/0286927 | A1* | 11/2010 | Horn et al. ....................... 702/19 |
| 2011/0136160 | A1* | 6/2011 | Sanchez et al. ................. 435/23 |
| 2012/0241603 | A1* | 9/2012 | Scigocki ....................... 250/282 |
| 2012/0245857 | A1 | 9/2012 | Lee et al. |
| 2012/0264154 | A1* | 10/2012 | Mann et al. ..................... 435/23 |

FOREIGN PATENT DOCUMENTS

| | | |
|---|---|---|
| EP | 2 309 262 | 4/2011 |
| WO | WO 87/00195 | 1/1987 |
| WO | WO 90/03430 | 4/1990 |
| WO | WO 91/17271 | 11/1991 |
| WO | WO 92/01047 | 1/1992 |
| WO | WO 92/09690 | 6/1992 |
| WO | WO 92/15679 | 9/1992 |
| WO | WO 92/18619 | 10/1992 |
| WO | WO 92/20791 | 11/1992 |
| WO | WO 93/01288 | 1/1993 |
| WO | WO 2006/096704 | 9/2006 |

OTHER PUBLICATIONS

Kirkpatrick, D. S., et al., 2005, "The absolute quantitation strategy: a general procedure for the quantification of proteins and post-translational modifications", Methods, vol. 35, pp. 265-273.*

Brun, V., et al., 2007, "Isotope-labeled protein standards toward absolute quantitative proteomics", Molecular and Cellular Proteomics, vol. 6, pp. 2139-2149.*

Woodcock, J., et al., 2007, "The FDA's assessment of follow-on protein products: a biological perspective", Nature Reviews—Drug Discovery, vol. 6, pp. 437-442.*

Amini, A., et al., 2008, "Quantitative analysis of polypeptide pharmaceuticals by matrix-assisted laser desorption/ionization tandem time-of-flight mass spectrometry", Journal of Pharmacological and Biomedical Analysis, vol. 46, pp. 411-417.*

Hanrieder, J., et al., 2008, "Proteomic analysis of human follicular fluid using an alternative bottom-up approach", Journal of Proteome Research, vol. 7, pp. 443-449.*

Jungblut, P. R., et al., 2008, "The speciation of the proteome", Chemistry Central Journal, vol. 2, No. 16, p. 1 through p. 10 of e-publication.*

Heudi, O., et al., 2008, "Towards absolute quantification of therapeutic monoclonal antibody in serum by LC-MS/MS using isotope labeled antibody standard and protein cleavage isotope dilution mass spectrometry", Analytical Chemistry, vol. 80, pp. 4200-4207.*

Liu, H., et al., 2008, "Heterogeneity of monoclonal antibodies", Journal of Pharmaceutical Science, vol. 97, pp. 2426-2447.*

Jenkins, N., et al., 2008, "Post-translational modifications of recombinant proteins: significance for biopharmaceuticals", Molecular Biotechnology, vol. 39, pp. 113-118.*

Ye, H., et al., 2008, "Qualitative and quantitative comparison of brand name and generic protein pharmaceuticals using isotope tags for relative and absolute quantification and matrix-assisted laser desorption/ionization tandem time-of-flight mass spectrometry: studies of insulins", Analytical Biochemistry, vol. 400, pp. 46-55.*

Jenkins, N., et al., 2009, "Strategies of analysing and improving the expression and quality of recombinant proteins made in mammalian cells", Biotechnology Applied Biochemistry, vol. 53, pp. 73-83.*

Israel-Tomasevic, A., et al., 2009, "Targeting interferon subtypes in serum: a comparison of analytical approaches to the detection and quantitation of proteins in complex biological matrices", Journal of Proteome Research, vol. 8, pp. 3132-3140.*

Li, H., et al., 2009, "Pharmacological significance of glycosylation in therapeutic proteins", Current Opinion in Biotechnology, vol. 20, pp. 678-684.*

Yu, X. C., et al., 2009, "Identification of codon-specific serine to asparagine mistranslation in recombinant monoclonal antibodies by high resolution mass spectometry", Analytical Chemistry, vol. 81, pp. 9282-9290.*

Wen, D., et al., 2009, "Discovery and investigation of misincorporation of serine at asparagine positions in recombinant proteins expressed in Chinese hamster ovary cells", Journal of Biological Chemistry, vol. 284, pp. 32686-32694.*

Ye, H., et al., 2010, "Qualitative and quantitative comparison of brand name and generic protein pharmaceuticals using isotope tags for relative and absolute quantification and matrix-assisted laser desorption/ionization tandem time-of-flight mass spectrometry", Analytical Biochemistry, vol. 400, pp. 46-55.*

Ishihama, Y., et al., 2005, "Quantitative mouse brain proteomics using culture-derived isotope tags as intimal standards", Nature Biotechnology, vol. 23, No. 5, pp. 617-621.*

Ong, S.F., et al., 2006, "A practical recipe for stable isotope labeling by amino acids in cell culture (SILAC)", Nature Protocols, vol. 1, No. 6, pp. 2650-2660.*

Singh, S., et al. 2009, "FLEXIQuant: A novel tool for the absolute quantification of proteins and the simultaneous identification and quantification of potentially modified peptides", Journal of Proteome Research, vol. 8, No. 5, pp. 2201-2210.*

Pan, S., et al., 2009, "Quantitative proteomics analysis integrated with microarray data reveals the extracellular matris proteins, catenins, aand P53 binding protein are important for chemotherapy response in ovarian cancers", Omics: A Journal of Integrative Biology, vol. 13, No. 4, pp. 345-354.*

Bichio, C.C., et al., 2010, "A genetic engineering solution to the 'Arginine Conversion Problem' in stable isotope labeling by amino adds in cell culture (SILAC)", Molecular and Cellular Proteomlcs, vol. 9, No. 7, pp. 1567-1577.*

Sury, M.D., et al., 2010, "The SILAC fly allows for accurate protein quantification in vivo", Molecular and Cellular Proteomics, vol. 9, No. 10, pp. 2173-2183.*

Zhang, Y., 2011, "Liquid chromatography/tandem mass spectrometry based targeted proteomics quantification of P-glycoprotein in various biological samples", Rapid Communications in Mass Spectrometry, vol. 25, No. 12, pp. 1715-1724. ePublication May 19, 2011.*

Kim, J.-S., et al., 2011, 18O-labeled proteome reference as global internal standards for targeted quantification by selected reaction monitoring-mass spectrometry, Molecular and Cellular Proteomics, vol. 10, No. 12, M110.007302 (13 pages).*

Garcia-Santamarina, S., et al., 2011, "The oxidized thiol proteome in fission yeast—Optimization of an ICAT-based method to identify H2O2-oxidized proteins", Journal of Proteomics, vol. 74, No. 13, pp. 2476-2486.*

Barbas, et al., "Assembly of Combinatorial Antibody Libraries on Phage Surfaces: The Gene III Site", *PNAS*, 88(18):7978-7982 (1991).

Bird, et al., "Single-Chain Antigen-Binding Proteins", *Science*, 242(4877):423-426, (1988).

Gram, et al., "In Vitro Selection and Affinity Maturation of antibodies from a Naïve combinatorial Immunoglobulin Library", *PNAS*, 89(8):3576-3580 (1992).

Greiger, et al., "Use of Stable Isotope Labeling by Amino Acids in Cell Culture as a Spike-In Standard in Quantitative Proteomics", *Nature Protocols*, 6(2):147-157 (2011).

Holliger, et al., "Diabodies": Small Bivalent and Bispecific Antibody Fragments, *PNAS*, 90(14):6444-6448 (1993).

Huse, et al., "Generation of a Large Combinatorial Library of the Immunoglobulin Repertoire in Phage Lambda", *Science*, 246(4935):1275-1281 (1989).

Huston, et al., "Protein Engineering of Antibody Binding Sites: Recovery of Specific Activity in an Anti-Digoxin Single-Chain Fv Analogue Produced in *Escherichia coli*", *PNAS*, 85(16):5879-5883 (1988).

(56) References Cited

OTHER PUBLICATIONS

International Search Report and Written Opinion for PCT/US2011/066003, dated Jul. 18, 2012 (corresponds to U.S. Appl. No. 13/332,077).

International Search Report for PCT/US2011/040669, dated Oct. 27, 2011 (corresponds to U.S. Appl. No. 13/161,907).

Manuilov, et al., "Comparability Analysis of Protein Therapeutics by Bottom-UP LC-MS with Stable Isotope-Tagged Reference Standards", *MABS*, 3(4):387-395 (2011).

Urlaub, et al., "Isolation of Chinese Hamster Cell Mutants Deficient in Dihydrofolate Reductase Activity", *PNAS USA*, 77(7):4216-4220 (1980).

Hanke, et al., :Absolute SILAC for accurate quantitation of proteins in complex mixtures down to the attomole level, *Journal of Proteome Research*, 7:1118-1130 (2008).

Liu, et al., "Proteome in vivo labeling using SILAC technology", *Chemistry of Life*, 29(3):427-430 (2009) (English Abstract only on p. 430).

Liffers ,e t al., "Stable isotope labeling by amino acids in cell culture (SILAC) a primer", *ISOTECH® Stable Isotopes*, Retrieved on line at www.sigmaaldrich.com/chin-mainland/zh/techincal-documents/articles/stable-isotopes/stable-isotope-labeling-by-amino-acids.html; pp. 1-4 (2008).

Ong, et al., "A practical recipe for stable isotope labeling by amino acids in cell culture (SILAC)", *Nature Protocls*, 1(6):2650-2660 (2006).

* cited by examiner

20% Mutant

| Unlabeled Peptides | | Labeled Peptides | | |
| --- | --- | --- | --- | --- |
| m/z | Abundance | m/z | Abundance | Unlabeled / Labeled |
| 1070.5072 | 119000 | 1073.5171 | 120000 | |
| 1071.0085 | 136000 | 1074.0185 | 127000 | |
| 1071.5093 | 90300 | 1074.5191 | 81200 | |
| 1072.0098 | 44100 | 1075.0199 | 38800 | |
| 1072.5109 | 18400 | 1075.5203 | 15900 | |
| Sum of Unlabeled | 408000 | Sum of Labeled | 383000 | 1.07 |

0% Mutant

| Unlabeled Peptides | | Labeled Peptides | | |
| --- | --- | --- | --- | --- |
| m/z | Abundance | m/z | Abundance | Unlabeled / Labeled |
| 1070.5085 | 113000 | 1073.5184 | 114000 | |
| 1071.0097 | 129000 | 1074.0197 | 120000 | |
| 1071.5108 | 85700 | 1074.5208 | 76300 | |
| 1072.0112 | 42700 | 1075.0214 | 36400 | |
| 1072.512 | 17600 | 1075.5218 | 14900 | |
| Sum of Unlabeled | 388000 | Sum of Labeled | 362000 | 1.07 |

*Fig. 4*

20% mutant

| Unlabeled Peptides | | Labeled Peptides | | |
|---|---|---|---|---|
| m/z | Abundance | m/z | Abundance | Unlabeled / Labeled |
| 835.1521 | 58000 | 839.667 | 83200 | |
| 835.4024 | 109000 | 839.9174 | 135000 | |
| 835.6528 | 115000 | 840.1677 | 130000 | |
| 835.903 | 88600 | 840.418 | 92600 | |
| 836.1534 | 54600 | 840.6681 | 54600 | |
| 836.4038 | 29000 | 840.9176 | 29100 | |
| 836.6539 | 14200 | 841.1666 | 15000 | |
| 836.9044 | 6610 | 841.4146 | 8040 | |
| Sum of Unlabeled | 475000 | Sum of Labeled | 547000 | 0.87 |

0% Mutant

| Unlabeled Peptides | | Labeled Peptides | | |
|---|---|---|---|---|
| m/z | Abundance | m/z | Abundance | Unlabeled / Labeled |
| 835.1544 | 64200 | 839.6692 | 71800 | |
| 835.4047 | 120000 | 839.9197 | 116000 | |
| 835.6551 | 128000 | 840.1699 | 111000 | |
| 835.9054 | 97700 | 840.4203 | 79700 | |
| 836.1556 | 60800 | 840.6702 | 47000 | |
| 836.4059 | 32200 | 840.9197 | 25400 | |
| 836.6559 | 15800 | 841.1678 | 13500 | |
| 836.9062 | 7550 | 841.415 | 7470 | |
| Sum of Unlabeled | 526000 | Sum of Labeled | 472000 | 1.11 |

*Fig. 6*

| Measured Characteristic | SITRS | Conventional Method | |
|---|---|---|---|
| $(G0F)_{HEK} / (G0F)_{CHO} * 100\%$ | 67.69 ± 0.52 | 68.25 ± 2.24 | 2-AB labeling |
| $(G1F)_{HEK} / (G1F)_{CHO} * 100\%$ | 148.19 ± 2.76 | 157.91 ± 1.52 | 2-AB labeling |
| $(M5)_{HEK} / (M5)_{CHO} * 100\%$ | 39.35 ± 1.00 | 56.80 ± 8.51 | 2-AB labeling |
| $(\text{N-term Q})_{HEK} / (\text{N-term Q})_{CHO} * 100\%$ | 25.97 ± 0.70 | 23.61 ± 2.80 | Label-free MS |
| $(\text{N-term pE})_{HEK} / (\text{N-term pE})_{CHO} * 100\%$ | 107.06 ± 0.41 | 111.87 ± 0.60 | Label-free MS |
| $(\text{C-term K})_{HEK} / (\text{C-term K})_{CHO} * 100\%$ | 10.60 ± 0.30 | 8.74 ± 1.22 | Label-free MS |

*Fig. 16*

COMPARISON OF PROTEIN SAMPLES

RELATED APPLICATIONS

This application claims the benefit of priority of U.S. Provisional Application Ser. No. 61/355,269, filed Jun. 16, 2010 which is incorporated herein by reference in its entirety.

BACKGROUND OF THE INVENTION

The present invention relates to an analytical method of comparing two or more protein samples using bottom-up Liquid Chromatography-Mass Spectroscopy (LC-MS) with a Stable Isotope-Tagged Reference Standard (SITRS).

Peptide mapping with mass spectroscopy (MS) detection is used in protein analytics for confirmation of the primary sequences. Known analytical methods primarily qualitatively confirm the presence of expected peptides.

SUMMARY OF THE INVENTION

In one aspect, the invention is directed to a method of characterizing a protein sample, the method comprising: (i) providing a sample of a first protein, having a known amino acid sequence, wherein at least one amino acid in the first protein is replaced with an isotopically labeled amino acid; (ii) providing a sample of a second, unlabeled protein comprising an unlabeled amino acid corresponding to the isotopically labeled variant in the first protein; (iii) mixing the first sample and the second sample to form a mixture; (iv) subjecting the mixture to protein digestion to form a first digest; (v) subjecting the first digest to bottom-up Liquid Chromatography-Mass Spectroscopy to form a first spectra including one or more doublet or singlet peaks, each doublet peak indicating the presence of an isotopically labeled peptide from the first sample and a corresponding unlabeled peptide from the second sample and each singlet peak indicating presence of peptide with a mutation, modification, or impurity. In certain embodiments, the method further comprises the step of (vi) comparing the relative intensities of the peaks in the doublet to determine the relative amount of each peptide, wherein a 1:1 peak ratio indicates substantial identity of the first and second peptides and wherein a differential in peak intensity reflects the presence of a chemically distinct peptide. In another embodiment, the method further comprising the step of quantifying the amount of the chemically distinct peptide based in a relative reduction in peak intensity. In another embodiment, the method further comprising the step of (vii) subjecting the digest to tandem mass spectroscopy to determine the sequence of a peptide represented by a singlet peak in the spectra.

In another aspect, the present invention is a method of qualitatively detecting the presence of mutations, modifications or impurities in a protein sample. The method allows comparing two or more protein samples to each other by comparing each sample to a Stable Isotope-Tagged Reference Standard (SITRS) protein. The method includes providing a sample of a first protein wherein at least one amino acid in the first protein (SITRS), having a known amino acid sequence, is replaced with an isotopically labeled amino acid; providing a sample of an unlabeled protein including an unlabeled amino acid corresponding to the isotopically labeled amino acid in the first protein, mixing the first protein and the unlabeled protein standard to form a mixture, subjecting the mixture to digestion and the subsequent analysis by bottom-up Liquid Chromatography-Mass Spectroscopy to determine whether a spectra includes a doublet indicating the presence of that particular peptide in each protein. If the doublet peak is not observed, then a single peak may correspond to a peptide, resulting from one of the following possibilities: (1) the peptide does not contain the labeled amino acid; (2) the peptide contains a modification; (3) the peptide contains a mutation, insertion or deletion; (4) the peptide corresponds to an impurity, and does not contain amino acid sequence present in the protein sample. The single peaks can then be analyzed by MS/MS to reveal the sequence of the peptide and to determine which of the four possibilities listed above are present.

In another aspect, the present invention is a method of quantitatively determining the presence of mutations or modifications in a protein sample. The method includes providing a sample of a first protein (SITRS), having a known amino acid sequence, wherein at least one amino acid in the first protein is replaced with an isotopically labeled amino acid; providing a sample of an unlabeled protein sample including an unlabeled amino acid corresponding to the isotopically labeled amino acid in the first protein, mixing the first protein and the unlabeled protein sample to form a mixture, subjecting the mixture to digestion and the subsequent analysis by bottom-up Liquid Chromatography-Mass Spectroscopy to determine whether a spectra includes a doublet indicating the presence of that particular peptide in both the SITRS and the unlabeled protein samples, and to compare the intensities of the peaks in the doublet to determine the relative abundances of that particular peptide in each protein. Additional unlabeled protein samples can be compared among each other by first comparing to the same SITRS antibody as described above, and then comparing the results among each unlabeled protein sample.

These and other aspects of the invention will be understood and become apparent upon review of the specification by those having ordinary skill in the art.

BRIEF DESCRIPTION OF THE DRAWINGS

FIG. 4 is a table of monoisotopic peak intensities for HC(255-273) from FIG. 3 in accordance with the present invention.

FIG. 6 is a table of monoisotopic peak intensities for HC(218-247) from FIG. 5 in accordance with the present invention.

FIG. 16 is table of stable isotope-tagged reference standard (SITRS) results presented in FIG. 15B with conventional analyses in accordance with the present invention. Selected results of the SITRS analysis (n=6) of mAb-1 from batch 2 (CHO-produced) and batch 3 (HEK-produced) are compared to the results obtained by conventional methods (n=3).

DETAILED DESCRIPTION OF THE PREFERRED EMBODIMENTS

Figure 1:
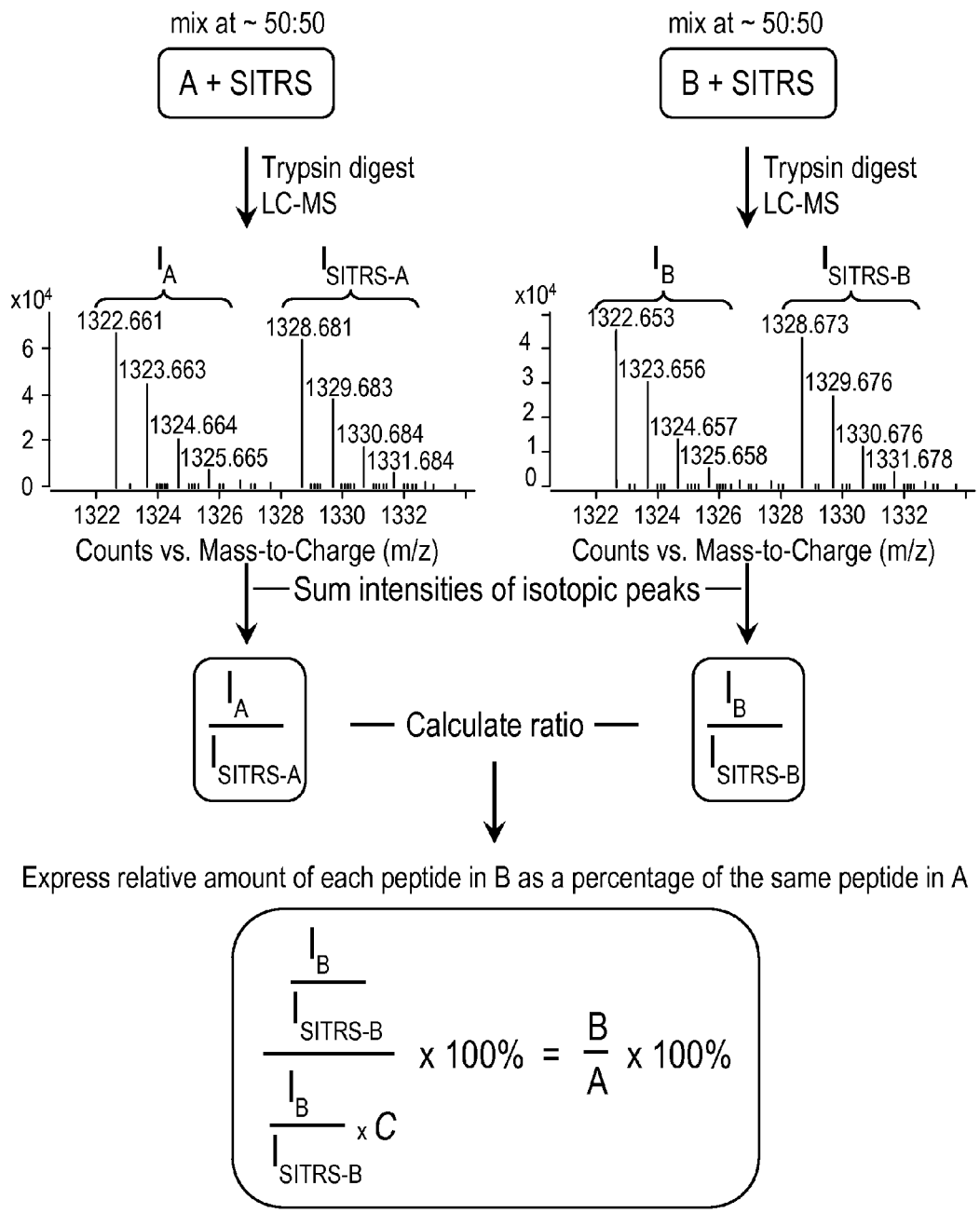
FIG. 1 is a schematic diagram of a SITRS experiment in accordance with the present invention.

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used on another embodiment to yield a still further embodiment.

Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

As used herein, the term "protein" or "polypeptide" refers to a polymer of 10 or more amino acids, e.g., 50, 100, 200, 300, 400, 500 or more amino acids. Exemplary proteins of the invention include, without limitation, recombinant proteins, biotherapeutic proteins, monoclonal antibodies and other antibodies, antibody-drug conjugates or other bioconjugates, imaging antibodies, fusion proteins, or PEGylated proteins.

As used herein, the term "monoclonal antibody" refers to a class of antibody proteins that bind to a specific target molecule (antigen) at one specific site (antigenic site).

The measurements achieved by the present invention take into account not only the masses of peptides generated during proteolytic digest, but also the abundance of each resulting peptide. Measuring of the abundance of peptides by MS is enabled by utilizing a SITRS sample that is mixed with an unlabeled protein prior to protein digest. As used herein, the term "SITRS sample" or "SITRS standard" means a protein (e.g., an antibody) of known sequence, labeled with a stable isotopically labeled variant of at least one amino acid present in the protein.

In one aspect, therefore, the present invention is a method of comparing two samples of proteins (e.g., antibodies) to qualitatively and/or quantitatively identify differences, such as mutations, modifications or impurities in the samples. The measurement may be conducted by utilizing a SITRS sample mixed with an unlabeled protein (e.g., unlabeled antibody) prior to protein digestion and LC-MS.

Introduction of a stable isotopically-labeled variant as an internal standard mitigates variation and artifacts from sample handling and MS detection that may affect quantitation. Examples of potential variations mitigated in accordance with the present invention include extent of protein digestion, formation of artifacts due to sample handling and/or variations in the ionization efficiency during MS detection. By utilizing the present method, such parameters may be normalized with respect to the SITRS sample.

In one aspect, the present method includes preparing a labeled protein (the SITRS sample) and mixing the labeled protein with an unlabeled protein sample. The mixed sample may then be subjected to bottom-up LC-MS to qualitatively and/or quantitatively determine low-level mutations, modifications or impurities in the unlabeled sample. This analysis may also be used to determine poor choice of an expression cell line, inefficiencies in a growth media, inefficiencies in cell culture conditions, inefficiencies in a purification process, or inadequacy of a formulation buffer.

In one exemplary embodiment, unlabeled antibody is formed in an experimental growth media or produced by an experimental cell line/clone, the resulting unlabeled antibody is mixed with a SITRS sample, and then the mixed sample is subjected to protein digestion and bottom-up LC-MS, which may be used to determine whether the experimental growth media cell line/clone is acceptable for production of desired antibodies.

Under standard Reverse Phase-High Performance Liquid Chromatography (RP-HPLC) conditions, labeled and unlabeled peptides have nearly identical retention times and, therefore, migrate together. While not resolvable by chromatography, the labeled and unlabeled peptides are distinguishable by MS detection, yielding differences in Daltons (Da) equivalent to the number of labeled residues in the particular peptide. Accordingly, when the SITRS sample is mixed with an unlabeled antibody or other protein, doublets indicating a difference in Da will appear in the mass spectra, indicating incorporation of the labeled amino acids into the SITRS sample, and the presence of the peptide with the same amino acid sequence in both the SITRS sample and the unlabeled antibody. A SITRS sample in which the only difference from its unlabeled counterpart (in a 1:1 mix) is the presence of the labeled amino acids will produce doublets in which each peak has an identical intensity.

The SITRS sample may be prepared using methods known in the art in which heavy amino acids are used in place of standard amino acids. For example, when preparing a protein that includes arginine and lysine residues, the growth media may include arginine and lysine residues composed of six $^{13}C$ atoms instead of the naturally abundant $^{12}C$ atoms (Arginine-6 and Lysine-6).

Heavy isotope-labeled variants known in the art are contemplated as useful in accordance with the present invention. Those having skill in the art will recognize that the selection of the heavy isotope-labeled variants will depend on the protein being formed and the protein digestion that will be conducted on the protein in preparation for LC-MS detection. For example, when the protein being produced includes arginine and/or lysine and will be subjected to trypsin digest, a heavy arginine and/or lysine may be desirable. Similarly, when the protein being produced includes aspartic acid and will be subjected to endoproteinase AspN digestion, a heavy aspartic acid may be desirable. When the protein being produced includes a glutamic acid and will be subjected to endoproteinase GluC digestion, a heavy glutamic acid may be desirable. When the protein being produced includes a chain of aspartic acid—aspartic acid—aspartic acid—aspartic acid—lysine and will be subjected to enterokinase digestion, a heavy aspartic acid and/or heavy lysine may be desirable. When the protein being produced includes a chain of isoleucine—glutamic acid or aspartic acid—glycine—arginine and will be subjected to Factor Xa digestion, a heavy isoleucine, glutamic acid, aspartic acid, glycine, and/or arginine may be desirable. When the protein being produced includes a chain of arginine—X-X—arginine and will be subjected to furin digestion, a heavy arginine may be desirable. When the protein being produced includes a histidine—tyrosine linkage and will be subjected to genease I digestion, a heavy histidine and/or tyrosine may be desirable. When the protein being produced includes an amino acid having an aromatic side chain and will be subjected to chymotrypsin digestion, a heavy amino acid having an aromatic side chain may be desirable. When the protein being produced includes a lysine and will be subjected to Lys-C or Lys-N digestion, a heavy lysine may be desirable. When the protein being produced includes a methionine and will be subjected to CNBr digestion, a heavy methionine may be desirable. When the protein being produced includes an arginine and will be subjected to endoproteinase ArgC digestion, a heavy arginine may be desirable. The invention is not intended to be limited to particular isotopically labeled variants or particular methods of protein digestion and the isotopically labeled variants and methods can be varied depending on the protein.

The present invention may further include a protein purification step. Protein purification methods known in the art are contemplated as useful in accordance with the present invention and may be utilized. A protein purification step may be conducted prior to protein digestion and, in some embodiments, it may be desirable to conduct a protein purification step prior to mixing the samples. In other embodiments, it may be desirable to conduct a protein purification step after mixing samples, but prior to protein digestion.

In some embodiments, it may be desirable to denature, reduce, and/or alkylate the mixed sample prior to protein digestion. The denaturation, reduction and alkylation steps may be conducted by methods known in the art. For example, the denaturation step may be conducted with the use of dialysis, off-line solid-phase extraction (SPE), on-line SPE, or liquid chromatography (LC), such as Size Exclusion Chromatography-High Performance Liquid Chromatography (SEC-HPLC) or Reverse Phase-High Performance Liquid Chromatography (RP-HPLC). In the on-line SPE or LC method, flow-rate may be controlled, the ultra-violet (UV) signal may be monitored, and the fraction collection may be timed to collect only the purified protein and not any residual buffer or other contaminants from the growth process or sample treatment.

Figure 3:
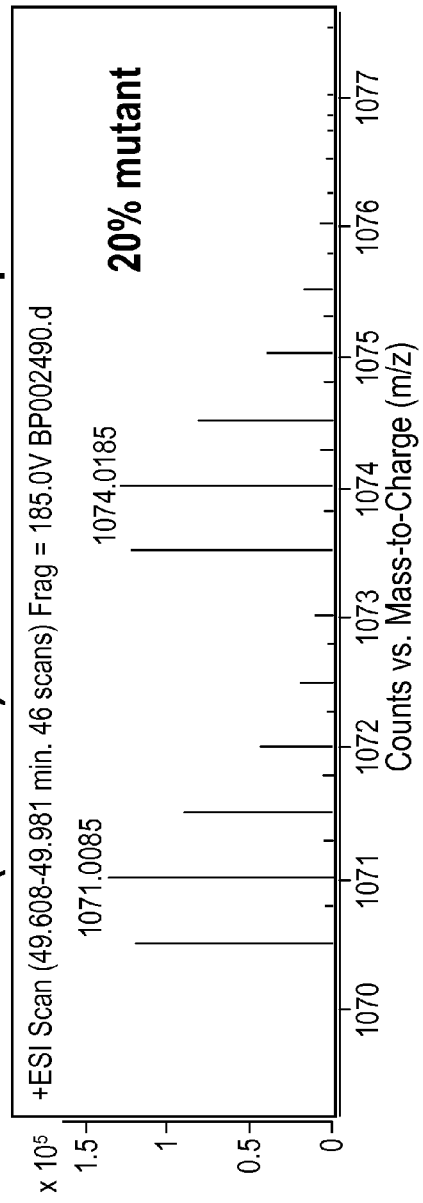
FIG. 3 is an extracted ion mass spectra for a SITRS experiment in which wt mAb-1 was compared to mAb-1 that was spiked with mutant to 20% (the wt HC(255-273) peptide that is present in both wt and mutant mAb is shown) in accordance with the present invention.
Figure 3:
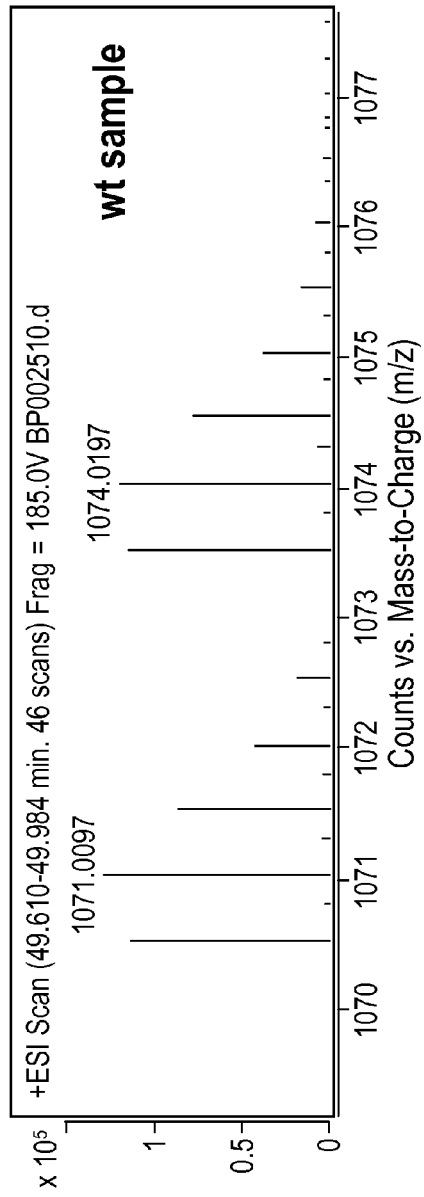
Figure 5:
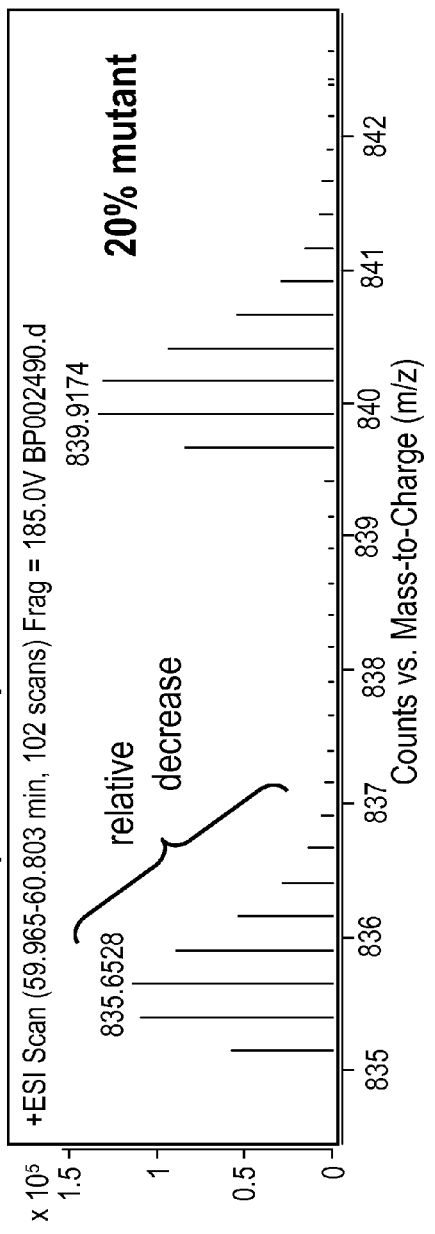
FIG. 5 is an extracted ion mass spectra for the SITRS experiment in which wt mAb-1 was compared to mAb-1 that was spiked with mutant to 20% (the wt HC(218-247) peptide that is modified in the mutant mAb is shown) in accordance with the present invention.
Figure 5:
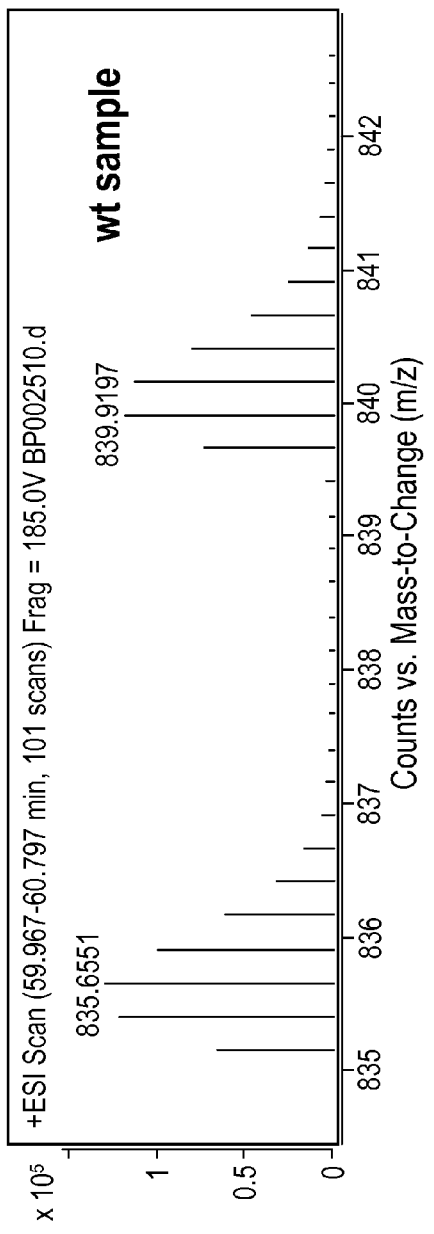

FIG. 1 provides a schematic SITRS analysis. FIGS. 3 and 5 show mass spectra from the SITRS analysis for two mixed samples, including an unlabeled MAb and its corresponding SITRS standard (no modification or mutation). As can be seen, a SITRS standard and an unlabeled MAb were mixed in a 1:1 ratio, subjected to protein (tryptic) digest, and then subjected to bottom-up LC-MS. The resulting mass spectra of peptides common to both the unlabeled sample and the SITRS standard are unique in that the mass to charge (m/z) peaks appear as doublets, due to the presence of labeled amino acids in the SITRS standard. Thus, a peptide that is identical in chemical composition to its SITRS counterpart and is present in the same amount as its SITRS counterpart will have an intensity that is equal to that of the standard (in a 1:1 mix) (see, e.g., FIG. 3).

Peptides whose population is partially composed of point mutants or site-specifically modified molecules, such as, for example, deamidation, N-terminal pyroglutamate, or differential glycosylation, will have a mass spectra where the intensity of the peak from the unlabeled sample is reduced compared to a SITRS standard by an amount that reflects the abundance of the chemically distinct peptide as can be seen in FIG. 5. Accordingly, by mixing a SITRS standard with an unlabeled protein preparation and subjecting the mixed sample to protein digestion and bottom-up LC-MS, the presence of mutations, modifications and/or site-specifically modified molecules in the unlabeled protein preparation may be identified and quantitated.

Antibody preparations from different cell lines may be compared utilizing the strategy described above. For example, the methods of the invention may be employed to qualitatively identify the presence of mutations and/or modifications in an unlabeled antibody grown in an experimental growth media or produced by an experimental clone/cell line. In this embodiment, a standard sample including at least one isotopically labeled amino acid (the "SITRS standard") is mixed with an unlabeled antibody produced by an experimental cell line. The mixed sample may then be subjected to protein digestion and bottom-up LC-MS to determine whether the experimental cell line is acceptable for production of desired antibodies.

Similarly to the embodiment discussed above, if the unlabeled antibody and the SITRS standard differ only in the presence of the labeled amino acid in the SITRS standard, then the two samples will migrate together through the MS and the only significant differences in the mass spectra will appear in the form of doublets indicating the presence of the labeled amino acids in the SITRS standard.

Figure 7:
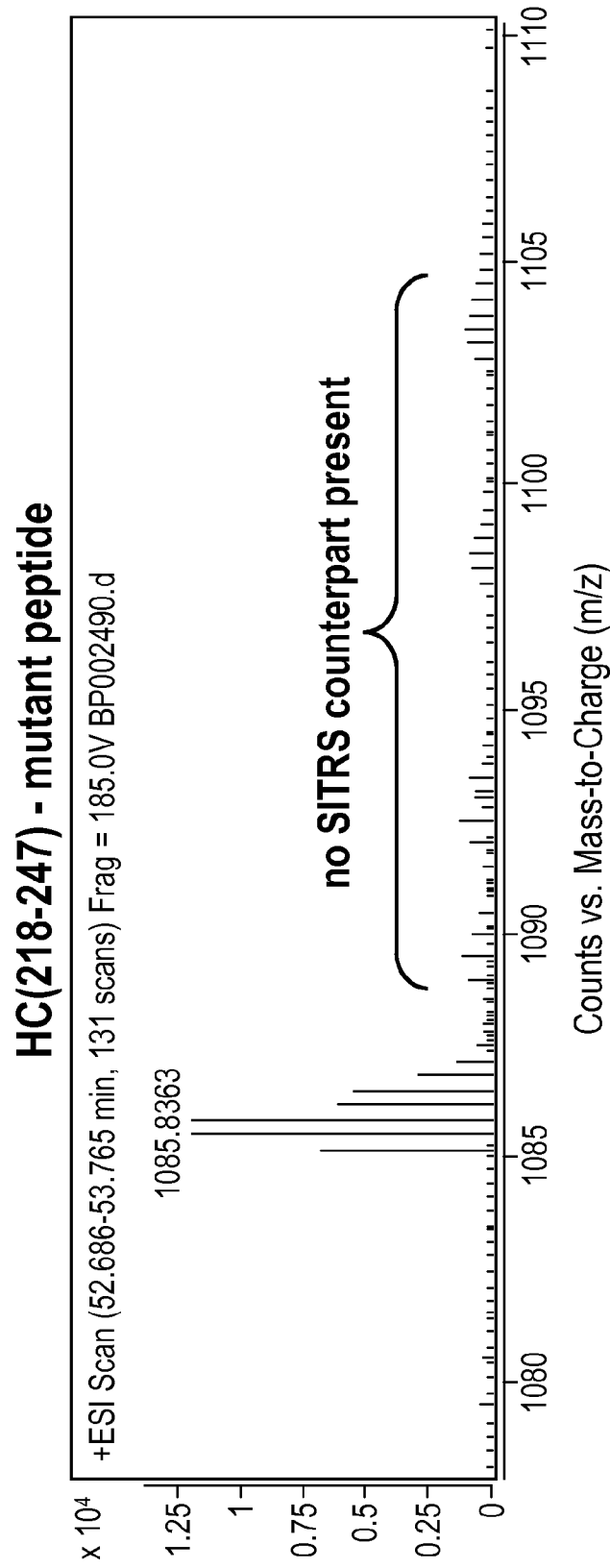
FIG. 7 is an extracted ion mass spectra for the SITRS experiment in which wt mAb-1 was compared to mAb-1 that was spiked with mutant to 20% (the mutated HC(218-247) peptide that is only present in the mutant mAb, and absent from the SITRS sample is shown) in accordance with the present invention.

If the doublet peak is not observed, then a single peak may correspond to a peptide resulting from one of the following possibilities: (1) the peptide does not contain the labeled amino acid; (2) the peptide contains a modification; (3) the peptide contains a mutation, insertion or deletion; (4) the peptide corresponds to an impurity and does not contain the amino acid sequence present in the antibody sample. The single peaks can then be analyzed by MS/MS to reveal the sequence of the peptide and to determine which of these four possibilities is present. FIG. 7, for example, shows the presence of the mutant peptide, which does not have a sister doublet. Accordingly, by mixing a SITRS standard with an unlabeled antibody and subjecting the mixed sample to protein digestion and bottom-up LC-MS, the presence of mutations, modifications and/or site-specifically modified molecules in the unlabeled antibody may be identified. Several unlabeled MAbs prepared by different cell lines can then be compared utilizing the same strategy described above in order to select the best clone.

In another aspect of the invention, the labeled SITRS standard enables quantitation of a protein by mass spectrometry, via comparison of the intensity of the m/z peak of each labeled SITRS standard peptide relative to that of its corresponding unlabeled peptide of unlabeled sample in each doublet. This in turn allows the comparison of all peptides spanning nearly an entire protein sequence. Several unlabeled proteins can then be compared to each other utilizing the strategy described above.

In this aspect of the invention, an unlabeled protein is prepared. Additionally, a SITRS standard corresponding to the unlabeled MAb is obtained. The unlabeled protein and the SITRS standard should be substantially identical and, if mixed, should show a 1:1 doublet in the MS, such as that seen in FIG. 1. To quantify the presence of any mutations or modifications in the unlabeled protein, the corresponding SITRS standard is mixed with an unlabeled sample. The mixture of the corresponding SITRS standard and unlabeled sample may then be subjected to protein digest and bottom-up LC-MS. The resulting spectrum may then be analyzed to determine whether the intensities of the doublet peaks are the same.

Additionally, to verify that the unlabeled MAb and the SITRS standard are identical with the exception of the isotopically labeled variants in the SITRS standard, the unlabeled MAb and the SITRS standard may be mixed together, subjected to protein digestion, and subjected to bottom-up LC-MS. The resulting mass spectral pattern should result in a substantially 1:1 peak as seen in FIG. 1. Peptides whose population is partially composed of point mutants or site-specifically modified molecules (such as deamidation, N-terminal pyroglutamate or differential glycosylation) however, will have a mass spectrum where the intensity of the peak from the unlabeled standard sample is reduced compared to the SITRS standard by an amount that reflects the abundance of the chemically distinct peptide (FIG. 1).

When comparing two unlabeled protein samples to each other, for example unlabeled sample A to unlabeled sample B, it might be necessary to further minimize variations that may arise from pipetting errors and MS detection. In order to minimize these variations, the ratios of the unlabeled sample A to the SITRS standard may be compared with those of the unlabeled sample B to the SITRS standard, as shown in Equation 1. The resultant value is called the SITRS Value (SV).

$$SV = \frac{I_A}{I_{SITRS-A}} \Big/ \frac{I_B}{I_{SITRS-B}} \times c = \frac{I_A}{I_B} * \frac{I_{SITRS-B}}{I_{SITRS-A}} \times c \quad \text{(Eq. 1)}$$

In Equation 1, $I_A$ is the peak intensity of the unlabeled sample A, $I_{SITRS-A}$ is the peak intensity of the SITRS standard mixed with the unlabeled sample A, $I_B$ is the peak intensity of the unlabeled standard sample B, and $I_{SITRS-B}$ is the peak intensity of the SITRS standard mixed with the unlabeled standard sample B. The peak intensity ratio of the unlabeled sample A to the unlabeled standard sample B is converted to a percentage of the expected signal by multiplying by c, a constant that is experimentally determined by obtaining the average of the most similar ratios of $[(I_A/I_{SITRS-A})/(I_B/I_{SITRS-B})]$ according to equation 2. Common peptides between the two runs will have similar ratios while peptides bearing differences will have different ratios.

$$c = 100\%/\overline{\chi}\{(I_A/I_{SITRS-A})/(I_B/I_{SITRS-B})\}_{most\ similar} \quad \text{(Eq. 2)}$$

Alternatively, the ratios of the unlabeled sample A to the SITRS standard may be compared with those of the unlabeled sample B to the SITRS standard, as shown in Equation 3:

$$\frac{B}{A} \times 100\% = \frac{\frac{I_B}{I_{SITRS-B}}}{\frac{I_A}{I_{SITRS-A}} \times c} \times 100\% \quad \text{(Eq. 3)}$$

In Equation 3, A and B are the relative amounts of a peptide in sample A and the same peptide in sample B, respectively. $I_A$, $I_B$, $I_{SITRS-A}$ and $I_{SITRS-B}$ are intensities of m/z ion peaks for the same peptide in samples A, B, SITRS standard mixed with sample A and SITRS standard mixed with sample B, respectively. Constant c is a normalization factor that accounts for possible unequal addition of SITRS standard to sample A versus sample B. Specifically, c is a trimmed mean of B/A values that exclude outliers outside of the 95% confidence interval of B/A values for a set of peptides that typically do not undergo post-translational modifications. Thus, multiplication of $I_A/I_{SITRS-A}$ by c produces a result equal to the ratio of $I_B/I_{SITRS-B}$ for the majority of the peptides quantitated.

Thus, a single quantitation experiment may involve running at least two protein digests, one containing unlabeled sample A (for example, a well characterized reference antibody) and the SITRS standard and the other containing the unlabeled sample B (for example, an antibody sample in question) plus the SITRS standard.

The following examples describe exemplary embodiments of the invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples.

EXAMPLES

Unless otherwise indicated, the following materials and equipment were utilized in the present examples. The methods described herein are not, however, limited to methods utilizing only these materials and/or equipment:

Materials used for Chinese Hamster Ovary (CHO) cell media and amino acids include:

Lys/Arg dropout media, available from Invitrogen, Carlsbad, Calif.;

L-Arginine (Arg-6) monohydrochloride, available from Cambridge Isotope Laboratories, Andover, Mass., cat #CLM-2265-0.25 (MW 216.62);

L-Lysine (Lys-6) dihydrochloride, available from Cambridge Isotope Laboratories cat #CLM-2247-0.25 (MW 225.07);

L-Arginine monohydrochloride, available from Sigma, Milwaukee, Wis., cat #A5131-1G (MW 210.66); and L-Lysine monohydrochloride, available from Sigma, Milwaukee, Wis., cat #L5626-1G, (MW 182.65)

Milli-Q Water or equivalent.

Materials used for Protein A purification include:
rProtein A Sepharose Fast Flow, available from GE Healthcare, Wauwatosa, Wis. cat #17-1279-03;
1M tris buffered saline (Tris), pH 8.5;
1× phosphate buffered saline (PBS), pH 7.4;
Acetic acid;
Sodium chloride;
Poly-Prep Chromatography Columns; available from Bio-Rad, Hercules, Calif. cat #731-1550;
Vacuum manifold;
UV-Vis Spectrophotometer, model: Cary 50; available from Varian, Palo Alto, Calif.; and
Microcon YM-30, available from Millipore, Billerica, Mass. cat #42410.

Materials used for trypsin digestion in peptide mapping include:
Iodoacetic acid (IAA), available from Sigma; cat #14386-10G;
Dithiothreitol (DTT), available from Sigma; cat #D-9163;
Trypsin, available from Worthington, Lakewood, N.J. cat #TRSEQZ, 4.61 u/mgP;
1M Tris-HCl, pH 8.0;
1M Tris-HCl, pH 7.5;
Guanidine hydrochloride (Gua-HCl), available from Calbiochem, Gibbstown, N.J.; cat #369075;
5N hydrochloric acid (HCl); J T Baker, Phillipsburg, N.J.; cat #5618-02; and
0.22 μm (CA) sterile filter disposable unit, available from Corning Life Sciences; cat #430015.

SEC-HPLC system used for gel filtration to remove denaturants and other impurities:
Agilent 1200 Quaternary HPLC system, available from Agilent Technologies, Santa Clara, Calif.;
Agilent reservoir tray, available from Agilent;
Agilent G1311A quaternary pump, available from Agilent;
Agilent G1322A degasser (in-line), available from Agilent;
Agilent G1367B HiP-ALS high performance autosampler, available from Agilent;
Agilent G1316A TCC column compartment with temp control, available from Agilent;
Tosoh TSK-Gel SW3000$_{XL}$ guard column, 6.0 mm ID×40 mm L, 7 μm particle, available from Tosoh, Tokyo, Japan, cat #08543;
Agilent G1364C Analytical fraction collector, available from Agilent;
Agilent G1330B temp controller for fraction collector, available from Agilent;
Agilent G1365D MWD (UV-VIS detector), available from Agilent; and
Agilent Chemstation data acquisition system with computer, available from Agilent.

Materials used for peptide mapping by RP-HPLC with MS detection include:
Triflouroacetic acid (TFA); available from J T Baker; cat #9470-00;
Formic acid (FA); available from EMD Chemicals; cat #FX0440-5; and
Acetonitrile (ACN), HPLC-grade, available from Honeywell Burdick and Jackson, Morris Township, N.J., cat #AH015-4.

LC-MS system used for peptide mapping by RP-HPLC with MS detection:
Agilent reservoir tray, available from Agilent;
Agilent G1376A capillary binary pump, available from Agilent;
Agilent G1379B micro vacuum degasser (in-line), available from Agilent;
Agilent G1377A Micro WPS autosampler, available from Agilent;
Agilent G1330B FC/ALS Therm autosampler thermostat, available from Agilent;
Agilent G1316B TCC SL column compartment with temp control, available from Agilent;
Agilent G6510A-6510 Q-TOF LC/MS system, available from Agilent;
Higgins Analytical Proto 200 C18, 5 μm, 250×1.0 mm, cat #RS-2501-D185, available from Higgins Analytical, Mountain View, Calif. serial #157337;
Agilent MassHunter data acquisition system with computer, available from Agilent;
Agilent MassHunter Workstation Software Qualitative Analysis; Version B.03.00; with Bioconfirm, available from Agilent; and
Microsoft Excel 2003 software; available from Microsoft.

Example 1

In the present example, unlabeled and labeled monoclonal antibodies (MAbs) were produced in a chemically defined media that lacked arginine and lysine amino acids. The media was then supplemented with either unlabeled or labeled L-Arginine (Arg) and L-Lysine (Lys) to 3.97 mM and 5.95 mM, respectively. The unlabeled and labeled versions of an antibody were produced using standard methods known in the art, then stored at −80° C. until needed.

Protein A Purification of Labeled MAb-1 (SITRS) and Unlabeled MAb-1:

Column Packing rProtein A Sepharose Fast Flow was used to purify MAb-1 (labeled and unlabeled). The resin was resuspended by vigorous shaking. The Sepharose (1.65 mL, about 1.2 mL of resin) was transferred into a Bio-Rad Poly Prep column that contained 10 mL of 1×PBS (the bottom of the column was capped).

The resin was allowed to settle to the bottom. The cap was then opened and the buffer was allowed to flow through, but was stopped just before reaching the bed of the resin.

Protein A Purification

The resin was equilibrated by passing 20 mL of 1×PBS (about 2 column volumes) at a rate of ~3-5 mL/min. Sample (10 mL~10 mg) was applied onto the column at a rate of ~1 mL/min. 10 mg of labeled MAb-1 and 10 mg of unlabeled MAb-1 were processed.

The column was then rinsed with 4×10 mL (about 2 column volumes) of 1×PBS at a rate ~3-5 mL/min and the sample was eluted with 5 mL of 0.1 M acetic acid, 0.15M sodium chloride, pH 3.5 by gravity flow.

Sample Reconstitution

The $A_{280}$ of eluted MAb-1 was measured on a 10× dilution of the eluate. Specifically, 20 μL of protein was diluted to 200 μL by addition of 180 μL of 10 mM Tris, pH 8.0 buffer. The extinction coefficient of MAb-1 was 1.43 mL/mg*AU.

Eluted MAb-1 (5 mL) was neutralized with 0.5 mL of 1M Tris, pH 8.5, which brought the pH into 7-8 range and raised the final concentration of Tris in the sample to 100 mM.

The purified MAb-1 was further concentrated using a Microcon YM-30 centrifugal filter. Because the capacity of the filter was 0.5 mL, the concentration was performed in two stages. The samples were centrifuged for 10 to 15 minutes at 10,000 g to reduce the volume to about 0.25 mL (4× concentration). The final sample concentrations were 6.07 mg/mL for the unlabeled and 5.63 mg/mL for the labeled MAb-1. Samples were then frozen at −80° C.

Sample Preparation for the SITRS Experiment:

Samples were prepared according to the following procedures:
  Unlabeled MAb-1, MAb-2 (double-point mutant of MAb-1), HEK-derived MAb-1 and labeled MAb-1 samples were diluted with Milli-Q water to 4 mg/mL.
  MAb-1 (4 mg/mL) was mixed with its double-point mutant MAb-2 (4 mg/mL) to yield 20%, 10%, 5%, 2.5%, 1.25% and 0.625% MAb-2 mutant-spiked samples of MAb-1.
  MAb-1 and the mutant-spiked MAb-1 samples (25 μL of 4 mg/mL) were mixed with 25 μL of 4 mg/mL labeled MAb-1.
  MAb-1, (HEK-derived, 25 μL of 4 mg/mL) was mixed with 25 μL of 4 mg/mL labeled MAb-1.

Denaturation, Reduction and Alkylation of Samples

Each SITRS-spiked sample (25 μL) was added to 75 μL of 8M Guanidine-HCl, 0.1M Tris, pH 8.0. The samples were incubated at room temperature for 15 minutes.

Reduction was carried out by adding 1 μL of 1M DTT to each sample, followed by incubation at 37° C. for 30 min.

The samples were alkylated by adding 5 μL of 0.5M IAA, and then incubating at 37° C. for 30 min under a foil cover. After the incubation, excess IAA was inactivated by adding 1.5 μL of 1M DTT to each sample.

Gel Filtration of Denatured, Reduced and Alkylated Samples Using SEC-HPLC

Figure 8:
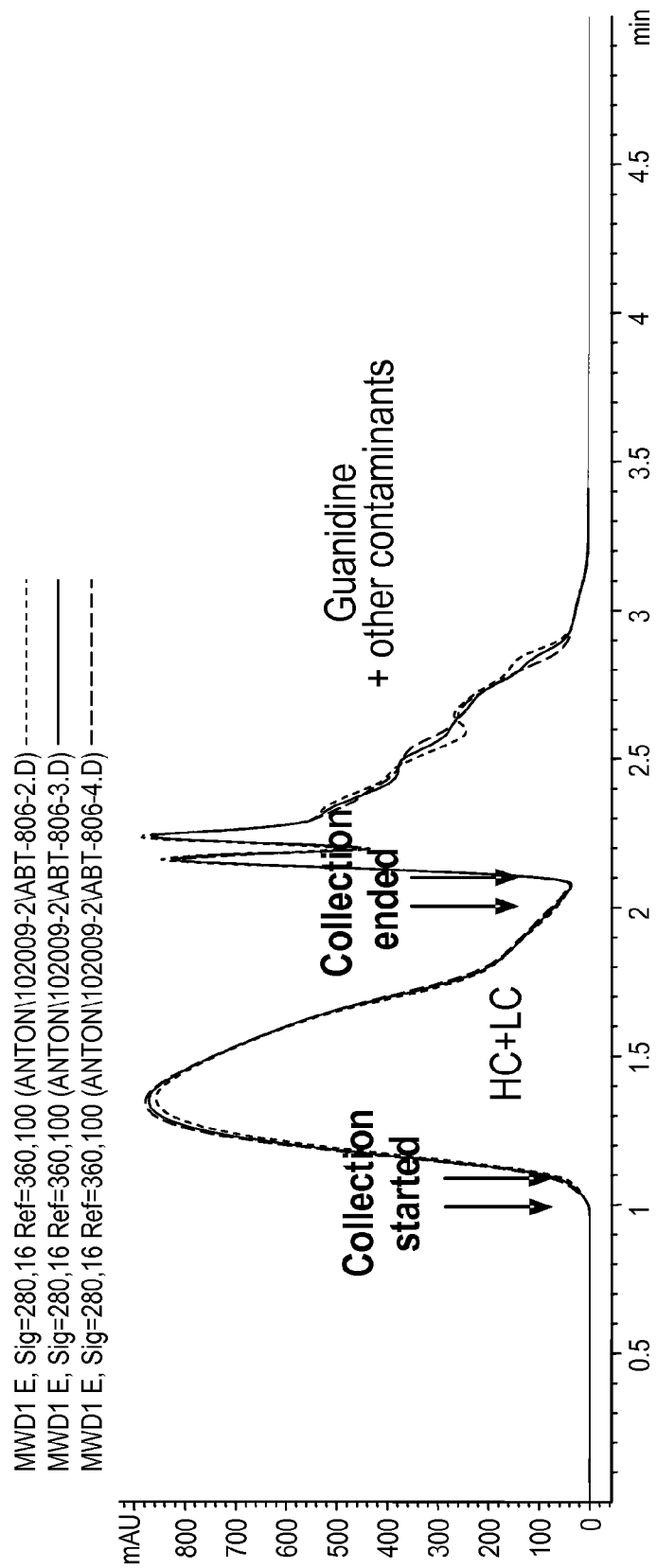
FIG. 8 is an LC chromatogram demonstrating antibody desalting utilizing the size exclusion chromatography-high performance liquid chromatography (SEC-HPLC) in accordance with the present invention.

The following conditions and materials were used for SEC-HPLC:
  Column: Tosoh TSKgel SW3000$_{XL}$ guard column, 6.0 mm ID×40 mm L, 7 μm particle
  Mobile Phase A: 10 mM Tris, pH 7.5
  Gradient: isocratic
  Flow rate: 0.25 mL/min, constant
  Autosampler and FC cooler temp: 4° C.
  Column oven temp: ambient
  Wavelength: 280 nm
  Total run time: 6 minutes
  Injection vol: 100 μL (about 100 μg)
  Fraction collection: based on time, collecting one fraction between 2 and 3 minutes at room temperature Gel Filtrations by SEC-HPLC 100 μL of each sample were injected, with washing steps in-between, into the SEC-HPLC. A typical chromatogram is shown in FIG. 8. 250 μL of purified sample was recovered by fraction collection; therefore the final concentration was about 0.4 mg/mL assuming that no sample loss occurred during the purification.

A column wash was performed between each sample run, by injecting 100 μL of cleaning solution (6M Gua-HCL in 75 mM Tris, pH 8.0). The column wash method was the same as above, except the flow rate was at 0.4 mL/min for 6 min and no fractions were collected.

Trypsin Digestion

8 μL of 0.25 mg/mL trypsin (resuspended in 1 mM HCl) were added to 200 μL (80 μg) of SEC-HPLC purified sample (1:40 enzyme to sample ratio by weight). Then, the mixture was incubated for 30 minutes at 37° C. After incubation, the reaction was quenched by addition of 4 μL of 1M HCl, to a final concentration of 20 mM. 20 μL (or about 8 μg) of sample were loaded onto HPLC for MS analysis.

LC-MS Analysis of Trypsin-Digested Antibodies

The following conditions and materials were used for LC-MS:
  Column: Higgins Analytical Proto 200 C18 RP column (5 μm, 200 Å, 1×250 mm)
  Mobile Phase A: 0.02% TFA, 0.08% formic acid in water
  Mobile Phase B: 0.02% TFA, 0.08% formic acid in ACN
  Gradient: binary
  Flow rate: 50 μL/min, constant
  Initial conditions: 2% B
  Autosampler cooler temp: 4° C.
  Column oven temp: 60° C.
  Total run time: 120 min
  Injection vol: 20 μL (8 μg of sample)
  Binary gradient program:

| Time (min) | % B |
|---|---|
| 0 | 2 |
| 10 | 2 |
| 90 | 55 |
| 100 | 98 |
| 110 | 98 |
| 112 | 2 |
| 120 | 2 |

The method diverted the eluent into waste for the first four minutes, and then directed it into the mass spectrometer. No MS/MS information was collected during the run to improve quantitation of the results.

The quantitation of peak intensities in each doublet was performed and corresponded to combined sequence of peptides spanning nearly the entire sequence of the antibody. Data was presented in a form of a "SITRS bar graph" as shown in FIGS. 10, 11, 12 and 13.

As can be seen from the above examples, the use of SITRS enables mining of MS-generated data for both qualitative and quantitative comparison of protein samples.

The above examples utilized the previously-discussed gel filtration by SEC-HPLC to remove denaturants and other impurities. As can be seen in FIG. 8, the eluent was monitored with an end result of a purified and less-dilute antibody sample than available in traditional desalting techniques. In addition, the nearly-complete elimination of guanidine salt from the sample permitted the significant shortening of the trypsin digestion time and, therefore, minimized sample-handling artifacts that could be introduced by prolonged incubation.

Three injections of MAb-1 onto the SEC-HPLC column were made to remove the guanidine and other contaminants. Absorbance at 280 nm was monitored throughout the run. Arrows in FIG. 8 indicate the start and the end of sample collection. The antibody was baseline resolved from the guanidine and other contaminants.

Figure 2:
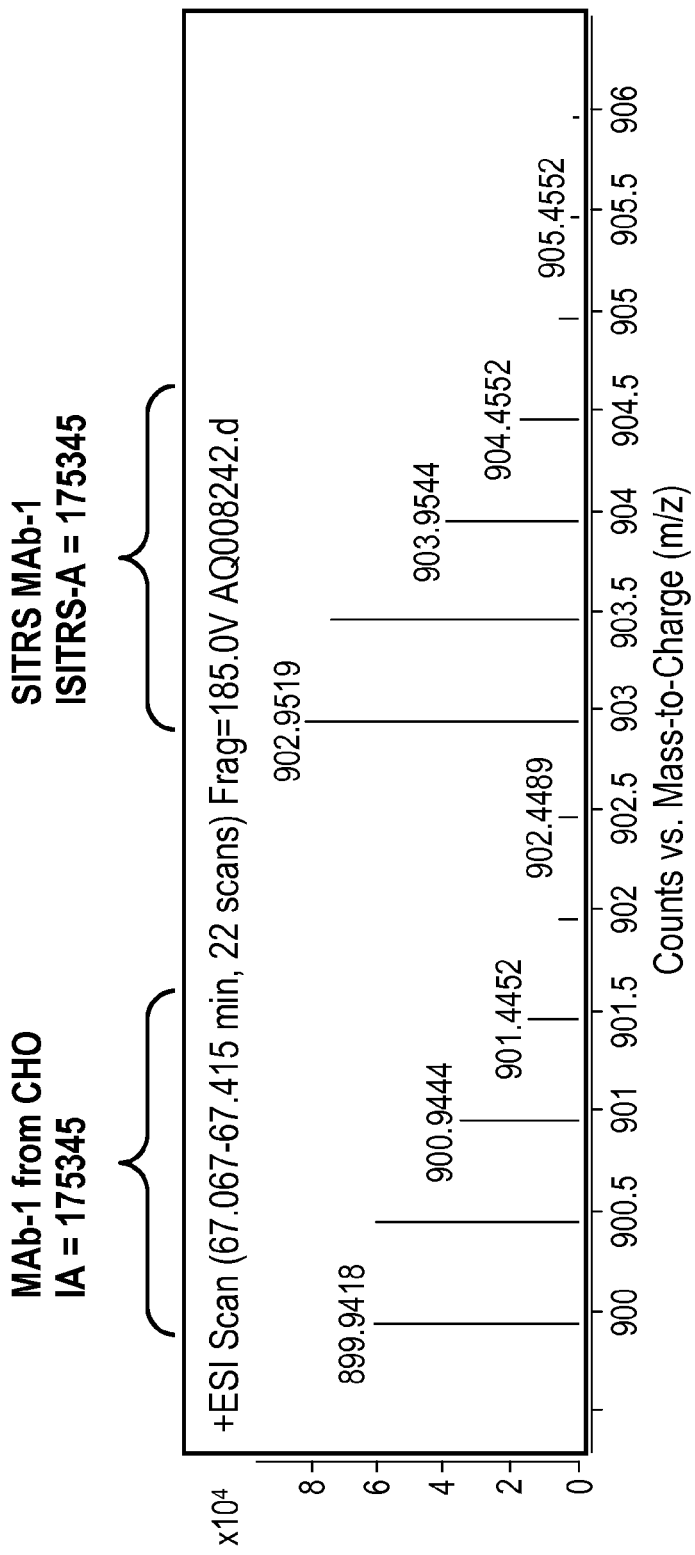
FIG. 2 is a representative mass spectrum of MAb-1 peptide generated by tryptic digest in the presence of its SITRS counterpart in accordance with the present invention.

Digesting a MAb-1 sample after removal of the guanidine and other contaminants in the presence of an equimolar amount of the SITRS standard resulted in mass spectra of peptides characterized by the expected doublets of appropriate signal intensity. FIG. 2 shows a typical mass spectrum of a peak from a tryptic digest of MAb-1, mixed in an equimolar ratio with the SITRS standard. In addition to the expected m/z peak of 899.9418 ([M+2H]+2 peak corresponding to peptide 127-142 of LC), plus monoisotopic peaks from naturally-occurring $^{13}$C-containing peptides for the unlabeled peptide, there is an additional set of peaks from the SITRS. The expected ratio of the peak intensities of MAb-1:SITRS is 1. The experimental ratio measurement, made by summing the peak heights of all relevant peaks, is 0.811. Calculation of the ratio for 11 peaks from the light chain in the chromatogram results in an average ratio of 0.823±0.014. This number was consistent across all 42 peptides examined, with a standard deviation of 2%. Without being bound by theory, it is believed the deviation from the expected ratio of 1 is likely due to a systematic factor such as pipetting errors in the initial protein concentration.

FIG. 3 shows another typical mass spectrum of a peak from a tryptic digest of MAb-1, mixed in an equimolar ratio with the SITRS standard. In addition to the expected m/z of 1070.5085 [M+2H]$^{2+}$ for the peptide 255-273 of heavy chain, plus monoisotopic peaks from naturally-occurring $^{13}$C-containing peptides for the unlabeled peptide, there is an additional set of peaks from the SITRS (m/z of 1073.5184 [M+2H]$^{2+}$ plus monoisotopic peaks from naturally-occurring $^{13}$C-containing peptides). The expected ratio of the peak intensities of MAb-1:SITRS is 1 (if samples were mixed 1:1 ratio and no modification of that particular peptide has occurred). The experimental ratio measurement, made by summing the peak heights of all relevant peaks, is 1.07 (FIG. 4). The same ratio was obtained for the same peptide HC(255-273) in 20% mutant-spiked MAb-1. This number was consistent across the majority of the peptides examined. However, when peptide HC(218-247) was examined (m/z of 835.15), the relative abundance of peak intensities corresponding to the unlabeled peptide in the 20% mutant-spiked MAb-1 was decreased relative to the labeled peptide of the same sequence in the SITRS standard (FIG. 5). The apparent change in peak intensity ratio has been quantitated and presented in FIG. 6. The experimental ratio measurement, made by summing the peak heights of all relevant peaks in the wild-type MAb sample (0% mutant), is 1.11, while the same measurement for the 20% mutant-spiked MAb-1 is 0.87. This decrease in the relative intensity of the unlabeled peptide HC(218-247) from the 20% mutant-spiked MAb-1 is consistent with this peptide being modified in the mutant of MAb-1 (MAb-2 sample).

In addition to quantitative data obtained from the SITRS experiment described above, qualitative information about the sample can also be obtained. FIG. 7 shows a set of monoisotopic peaks without a doublet. This peak corresponds to a peptide HC(218-247) from MAb-2 (double-point mutant of MAb-1) that is not present in a wild-type MAb-1.

Example 2

The presence of m/z peaks from the SITRS standard enables the quantitation of differences in abundance of a given peptide. This example details quantitation of the level of contamination of a sample of MAb-1 by an antibody other than MAb-1, e.g., MAb-2 antibody that has an amino acid sequence that does not fully match the sequence of MAb-1.

Figure 9A:
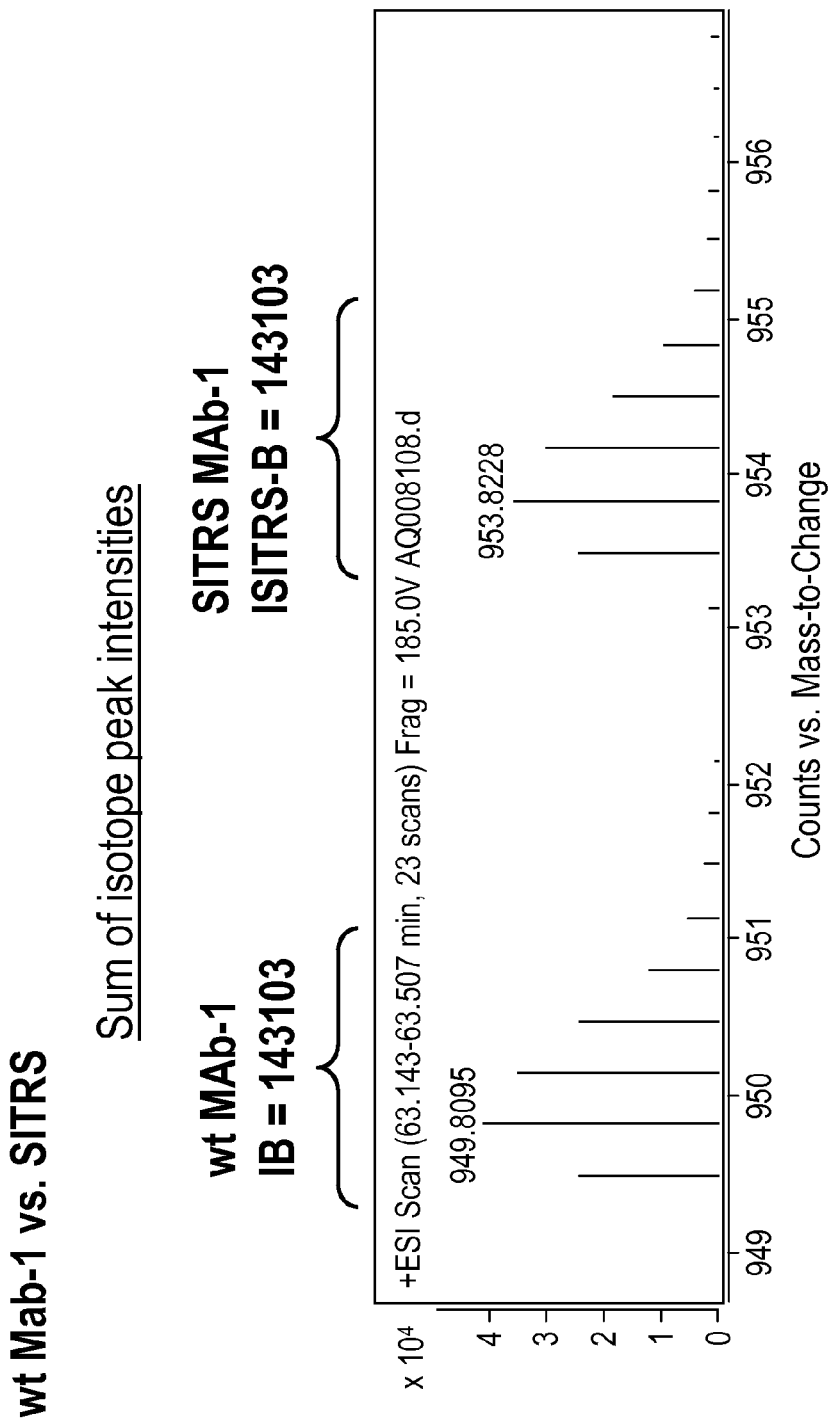
FIG. 9 is a comparison of mass spectra of a peptide from (A) pure unlabeled MAb-1 and (B) MAb-1 contaminated with 10% MAb-2. SITRS was mixed with each in a 1:1 ratio prior to tryptic digest and analysis in accordance with the present invention.
Figure 9B:
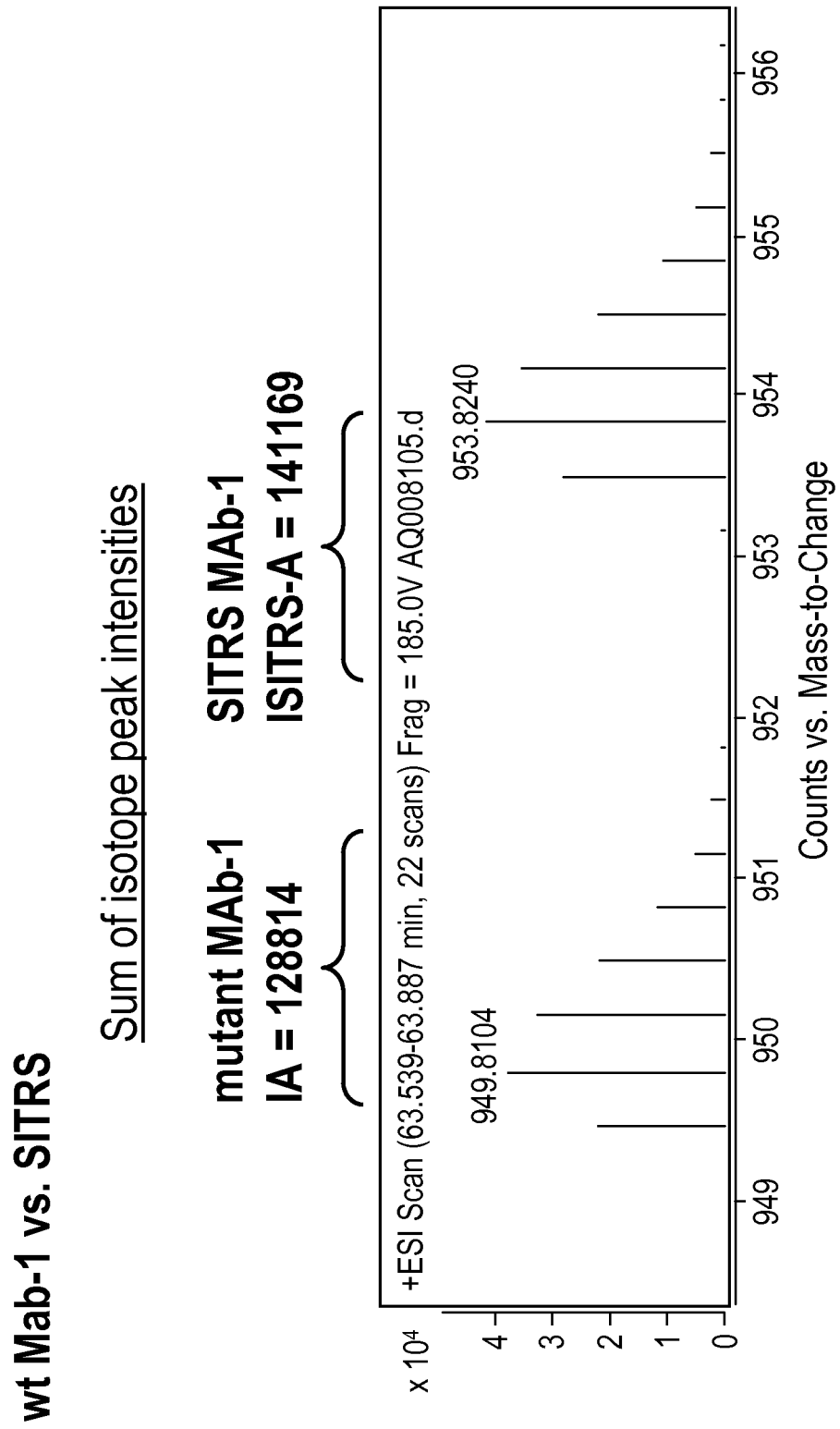
Figure 10:
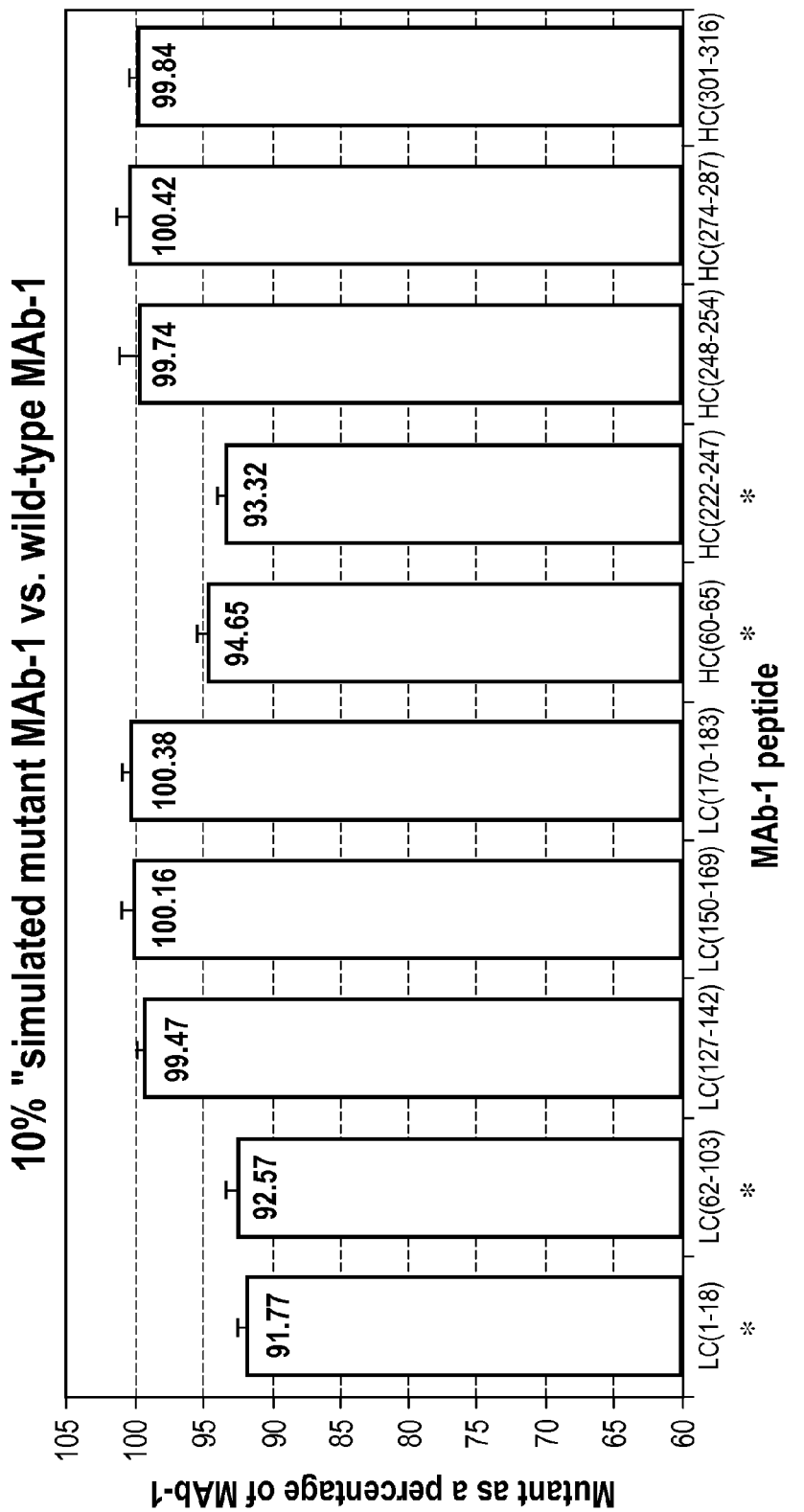
FIG. 10 is a graph depicting SITRS values for 6 peptides studied in the quantitation of a MAb-1 sample contaminated with 10% MAb-2 in accordance with the present invention.

In one experiment, a sample of MAb-1 was spiked with MAb-2 to a final concentration of 10% (90% MAb-1+10% MAb-2). This experiment was intended to simulate samples that contain varying amounts of an antibody that bears point mutations, a plausible scenario that may arise by accident or through natural biological processes during manufacturing. Being highly homologous, most peptides generated by tryptic digest are common between the two antibodies and were expected to yield a STIRS value (SV) of 100%. Six such peptides were selected for study. There are a few however, which differ by 1 or more amino acids and were expected to have an SV of 90%. FIG. 9 shows two mass spectra from one such "mutant" peptide. The first spectrum is from the unlabeled antibody standard (no contaminating MAb-2 was added) mixed with SITRS (FIG. 9A) and the second spectrum is from the unlabeled, contaminated sample containing 10% MAb-2 mixed with SITRS (FIG. 9B). The observed SV for this mutation-bearing peptide is approximately 93.3%. More broadly, peptides that are different between MAb-1 and MAb-2 have an average SV of 93%, while the common peptides had the expected value of approximately 100% (FIG. 10). The discrepancy was unaccounted for but, without being bound by theory, may be explained by errors in pipetting or concentration. Thus, the SITRS method was successfully used to identify point mutations in molecules at a level of 10% of total protein.

Figure 11:
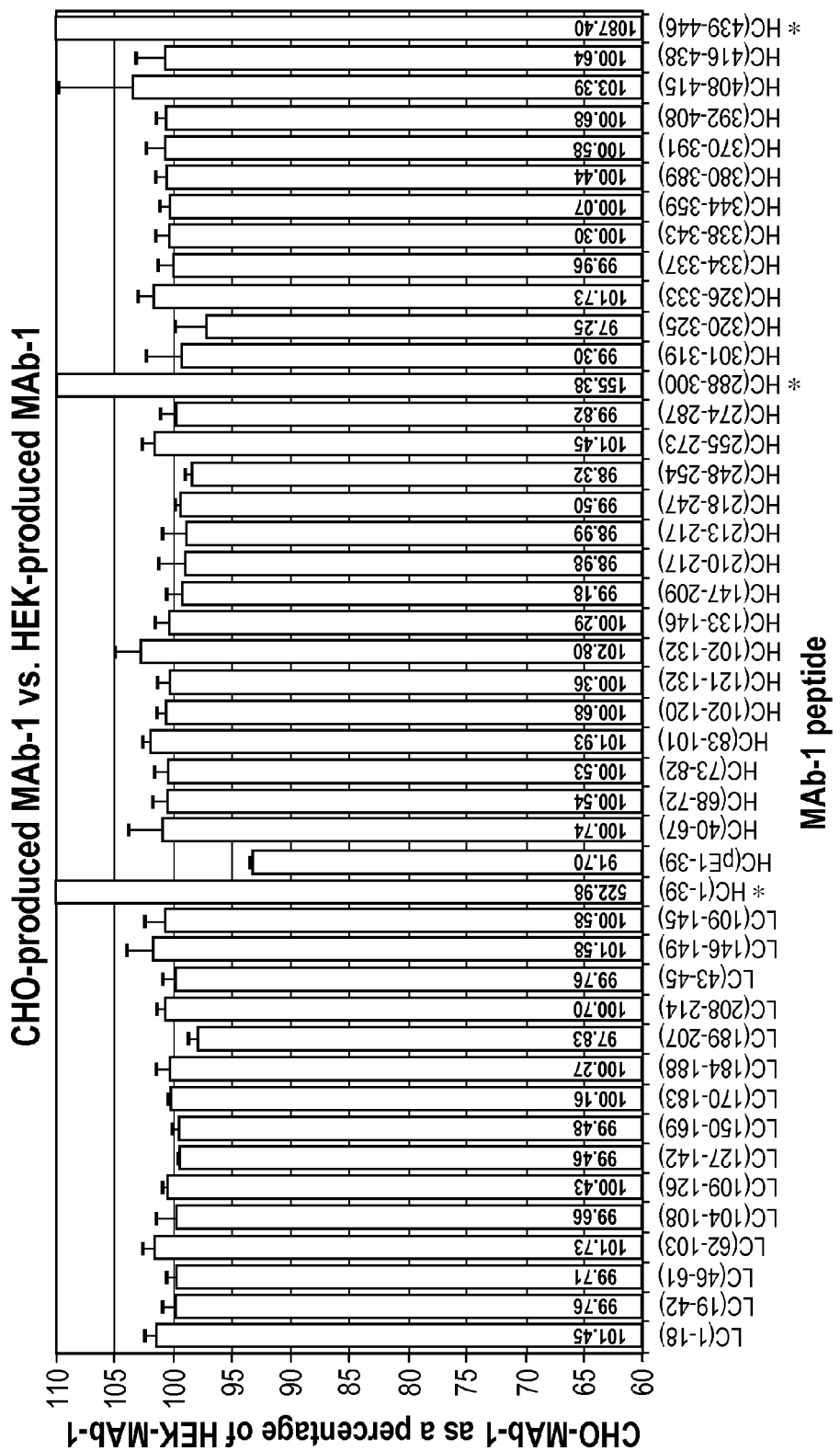
FIG. 11 is a comparison of SV from MAb-1 peptides derived from Human Embryonic Kidney 293 cells versus Chinese Hamster Ovary cells in accordance with the present invention.

FIG. 11 and Table 1 show data from a SITRS experiment using material derived from CHO and from 293 cell lines. 293-derived material has 20% less agalactosylated glycoform (NGA2F) glycosylation in the heavy chain than MAb-1 from CHO. Furthermore, the two batches also differ in the amount of C-terminal lysine on the heavy chain, as well as the amount of N-terminal pyroglutamate formation. Peptides bearing these modifications were readily apparent in the SITRS experiment by their dramatic differences in SV (columns marked with an asterisk in FIG. 11). Furthermore, peptides that were predicted to show no difference in levels of abundance (that is, all the common peptides) were similar in their SITRS ratios, with an average standard deviation for unmodified peptides of 1.4% (ranging from 0.22 to 6.31%).

TABLE 1

A comparison of modifications identified by SITRS versus standard methods

| Measured Characteristic | SITRS Method | Standard Method |
|---|---|---|
| (% NGA2F$_{CHO}$)/ (% NGA2F$_{293}$) | 1.554 | 61.67/39.35 = 1.567 |
| (% pyroglutamate$_{CHO}$)/ (% pyroglutamate$_{293}$) | 0.917 | 81.33/95.59 = 0.851 |
| (% C-terminal lysine)$_{CHO}$/ (% C-terminal lysine)$_{293}$ | 10.9 | 13.86/1.54 = 9.00 |

As can be seen, therefore, a novel method was devised using a stable isotope-tagged protein as an internal reference standard to quantitate differences amongst batches of a given protein. Uniform incorporation of lysine-6 and arginine-6 into MAb-1 was achieved by producing MAb-1 in a cell culture using lysine- and arginine-deficient chemically-defined media supplemented with the labeled amino acids. A comparison of unlabeled MAb-1 with its SITRS standard counterpart by mass spectrometry demonstrated that the data generated by this method is consistent, with a standard deviation of 2%. Application of the method to MAb-1 produced by a HEK 293 cell line correctly identified the peptides bearing differences in levels of modification, such as N-terminal pyroglutamate, C-terminal lysines, and NGA2F levels. Furthermore, the method was successfully used to identify the peptides bearing 1 amino acid difference between MAb-2 and MAb-1 at a level of approximately 10%.

Example 3

Figure 12:
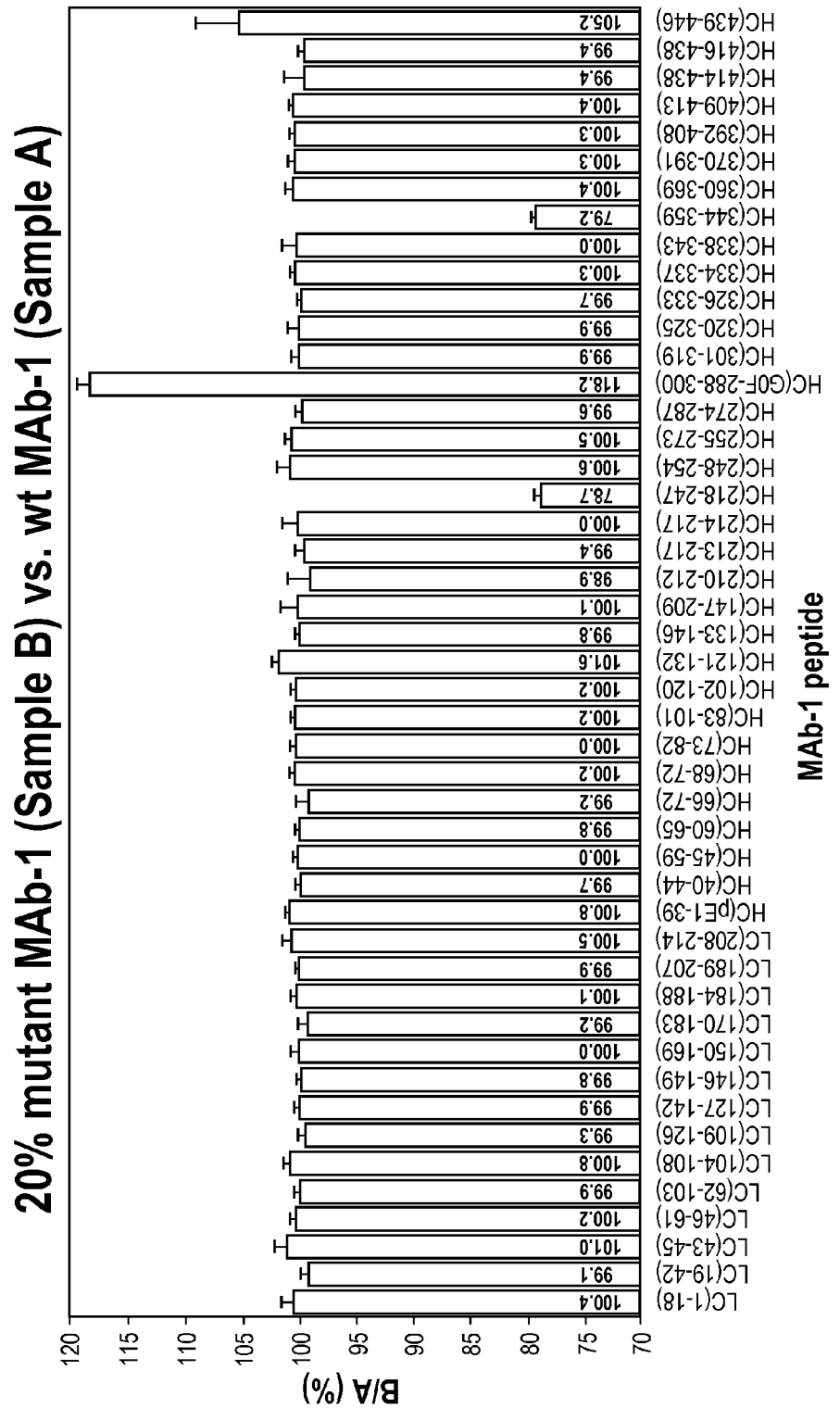
FIG. 12 is a SITRS bar graph for the SITRS experiment in which wt mAb-1 was compared to mAb-1 that was spiked with mutant to 20% in accordance with the present invention.
Figure 13:
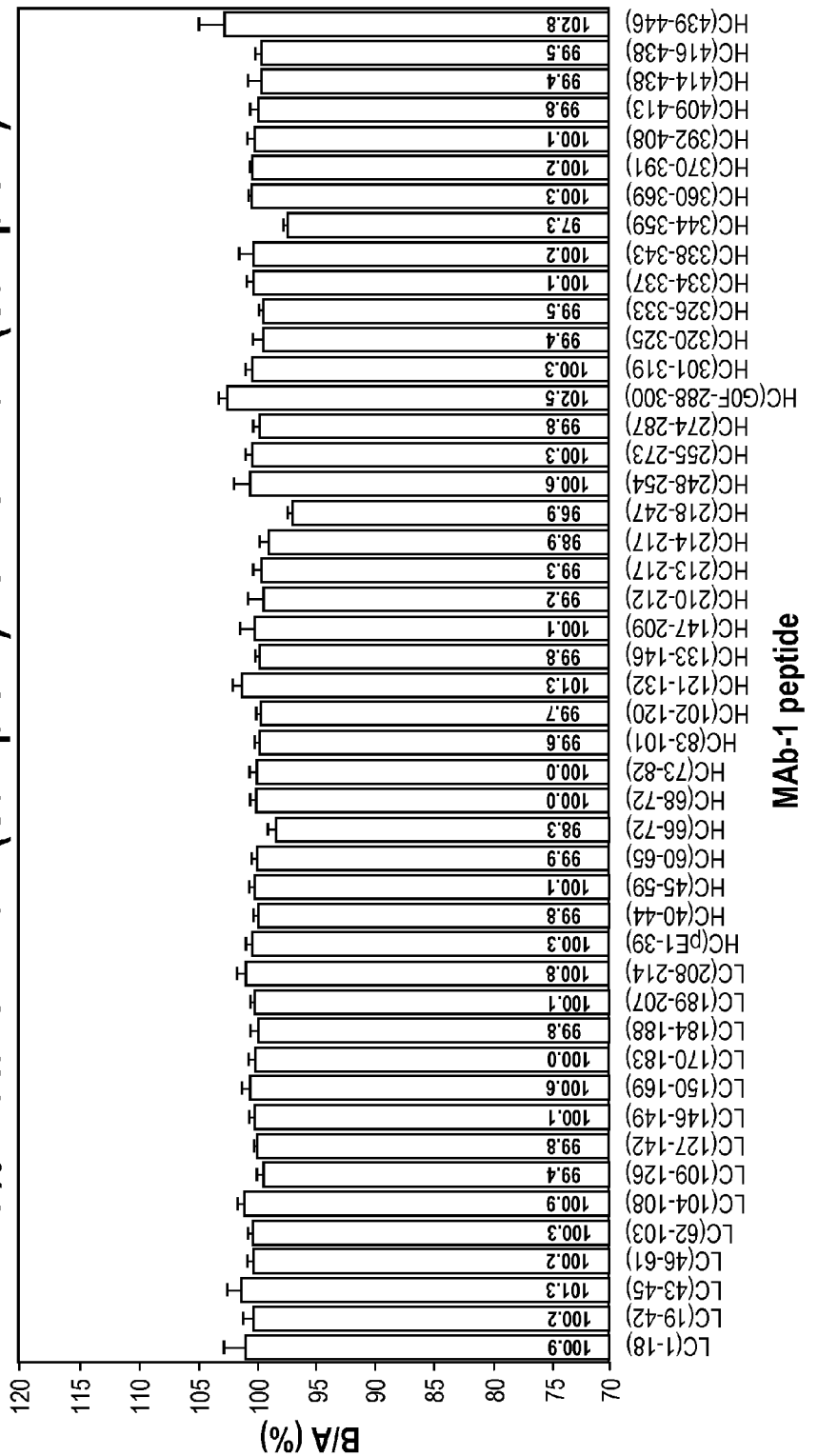
FIG. 13 is a SITRS bar graph for the SITRS experiment in which wt mAb-1 was compared to mAb-1 that was spiked with mutant to 2.5% in accordance with the present invention.
Figure 14:
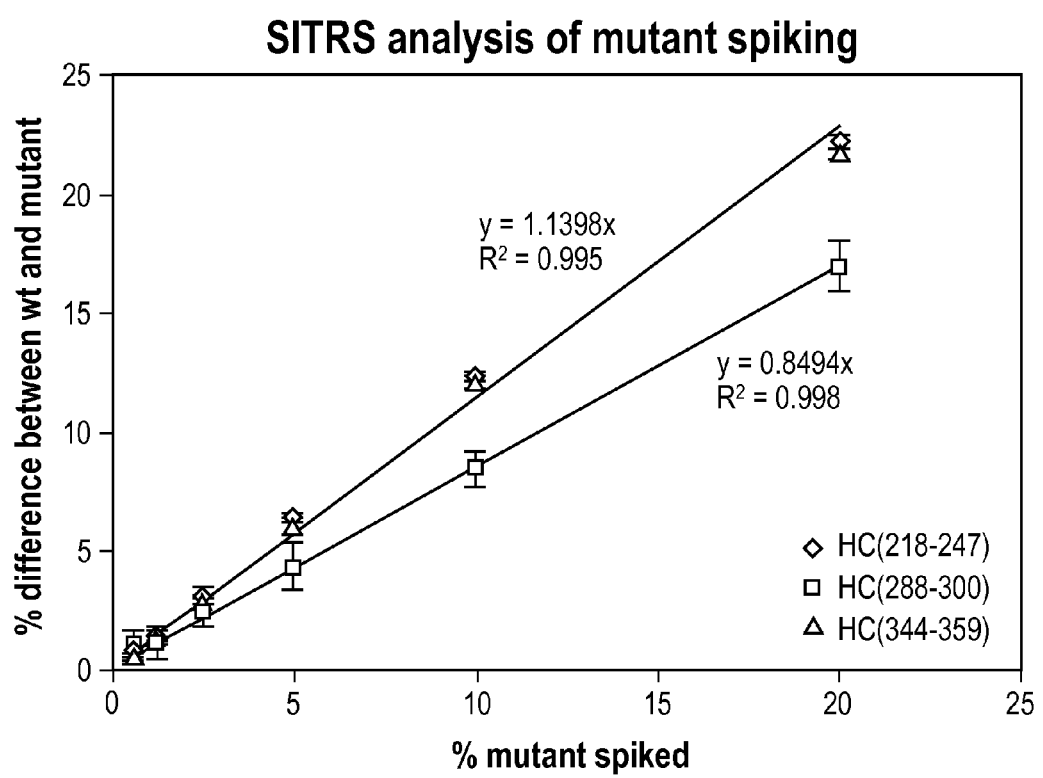
FIG. 14 is a plot of the amounts of peptides HC(218-247), HC(344-359) and HC(288-300) in the mutant-spiked antibody relative to that of the wild-type antibody as measured by the SITRS analysis of various mutant-spiked mAb-1 samples in accordance with the present invention.

In another experiment, a sample of MAb-1 was spiked with mutant MAb-1 containing 2 point mutations (MAb-2). Specifically, one mutation resides in peptide HC (218-247) and the other in HC (344-349). The mutant was added to a final concentration ranging from 20% (90% MAb-1+20% mutant MAb-1, FIG. 12) to 2% (98% MAb-1, 2% mutant MAb-1, FIG. 13). FIGS. 12 and 13 show that peptides which are common to both wild type and mutant MAb-1 have the expected value of approximately 100%. The two mutant peptides have the expected value of approximately 80% (FIG. 12) or 98% (FIG. 13). Glycopeptide HC (G0F-288-300) and HC (439-446) are also different between the two samples. This was expected as it was known that the glycopeptides and the C-terminal peptide in the two samples differed in their oligosaccharide composition and C-terminal lysine content, respectively. FIG. 14 shows the percent difference in levels of wild type peptides HC(218-247), HC(344-349) and HC(G0F-288-300) for various amounts of mutant MAb-1 spiked into wild-type MAb as measured by SITRS. The method responds linearly to the amount of mutant present and has a method detection limit of 2.4%.

Example 4

Figure 15A:
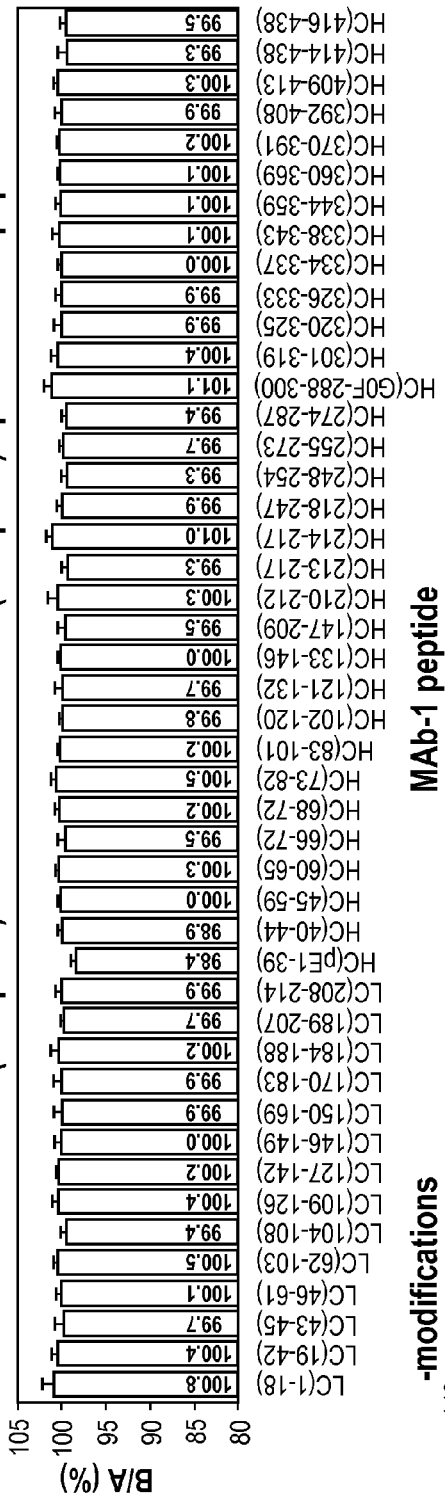
FIG. 15 is a SITRS bar graph for the comparison of batches of MAb-1 samples produced by two different cell lines using two different processes (CHO-produced (FIG. 15A) and HEK-produced (FIG. 15B)) in accordance with the present invention.
Figure 15A:
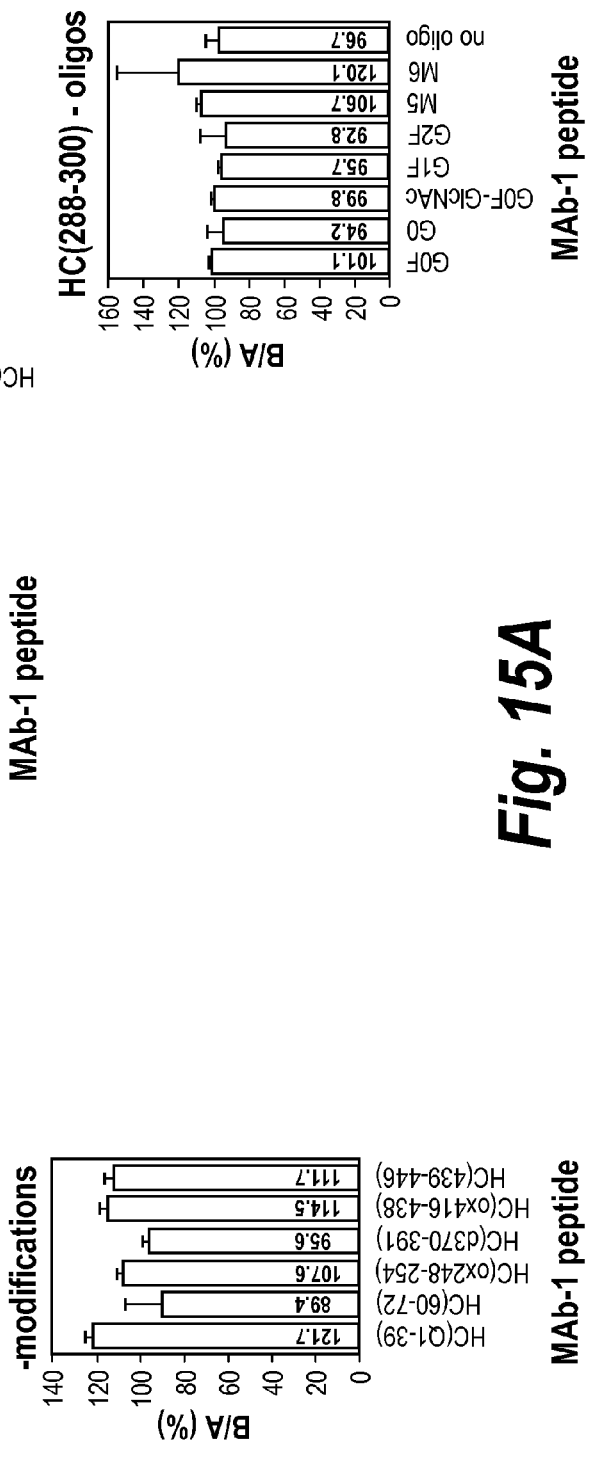
Figure 15B:
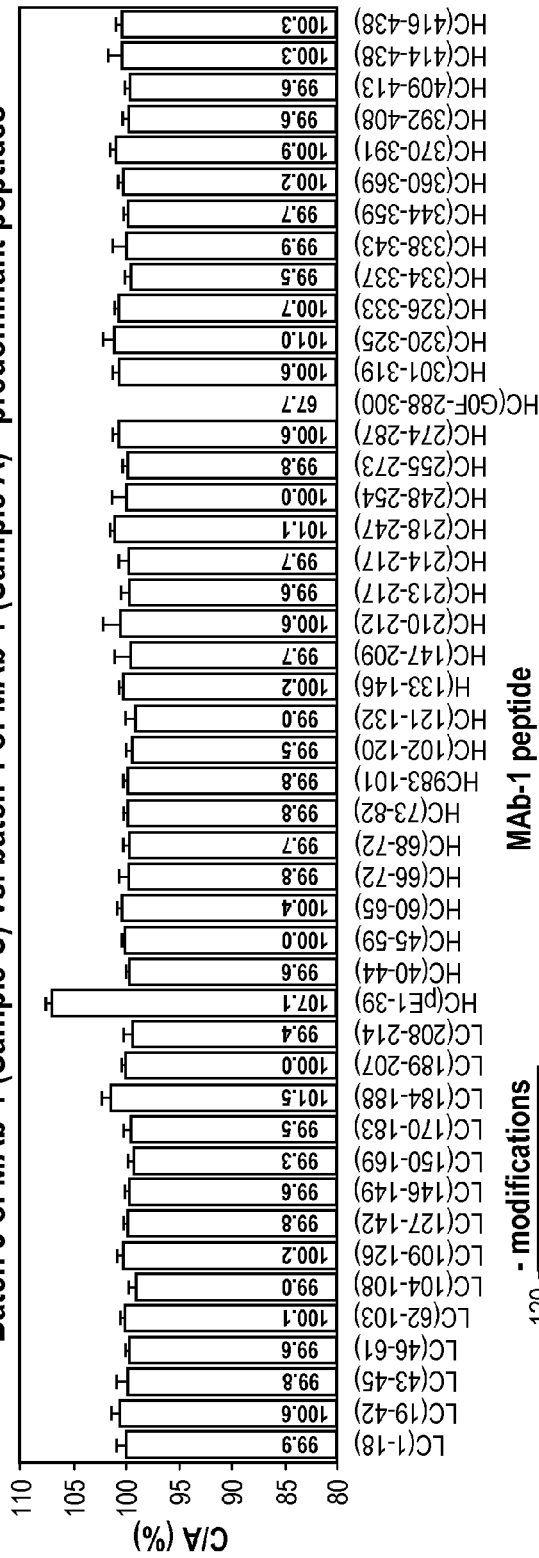
Figure 15B:
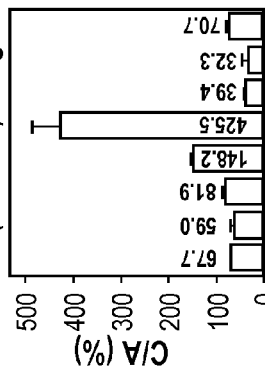
Figure 15B:
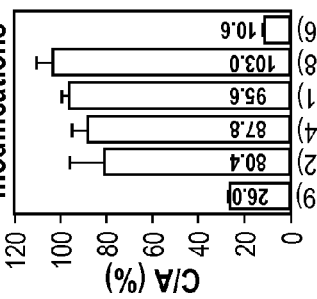

To further test the ability of the SITRS method to discriminate between samples, a change in manufacturing process was simulated by producing the mAb-1 in a HEK cell line. The SITRS analysis of the CHO- and HEK-derived mAb is shown in FIG. 15A and FIG. 15B, respectively. Three peptides immediately stand out from the analysis. First, HC(1-39), which bears an N-terminal pyroglutamate residue, is more abundant in the HEK sample by 7.1%. Consistent with this result, HC(1-39) bearing an N-terminal uncyclized glutamine residue is more abundant by 74% in the CHO-derived mAb. The second site of differentiation is in the C-terminal heavy chain peptide HC(439-446). This was due to minor differences in proteolytic processing of Lys446, a common post-translational event in mAbs. The third significant difference is in the relative abundance of various glycopeptides.

To verify these differences, the MAbs were deglycosylated with PNGase F and the oligosaccharides were quantitated by HPLC after labeling with 2-aminobenzoic acid. The differences in oligosaccharide content as determined by the SITRS method versus enzymatic digestion are summarized in FIG. 16. Also included in FIG. 16 is a comparison of the levels of N-terminal glutamine conversion and C-terminal lysine removal between the SITRS and label-free MS analyses, as determined by comparison of the intensities of de-charged and de-isotoped peaks via the MassHunter with Bioconfirm software package from Agilent. The results of these two orthogonal methods agree reasonably well, particularly for abundant peptides.

In contrast, two batches of the mAb that were produced by the same manufacturing process in CHO cells were shown to be very similar (FIG. 15A). Less than 3% difference was observed in the amount of N-terminal pyroglutamate in peptide HC(1-39). Similarly, the relative difference in HC(392-445) was only 3.3%. Unlike the batch produced in HEK cells, the two CHO-derived batches also showed comparable glycosylation patterns, a result that is supported by oligosaccharide profiling.

Example 5

Figure 17:
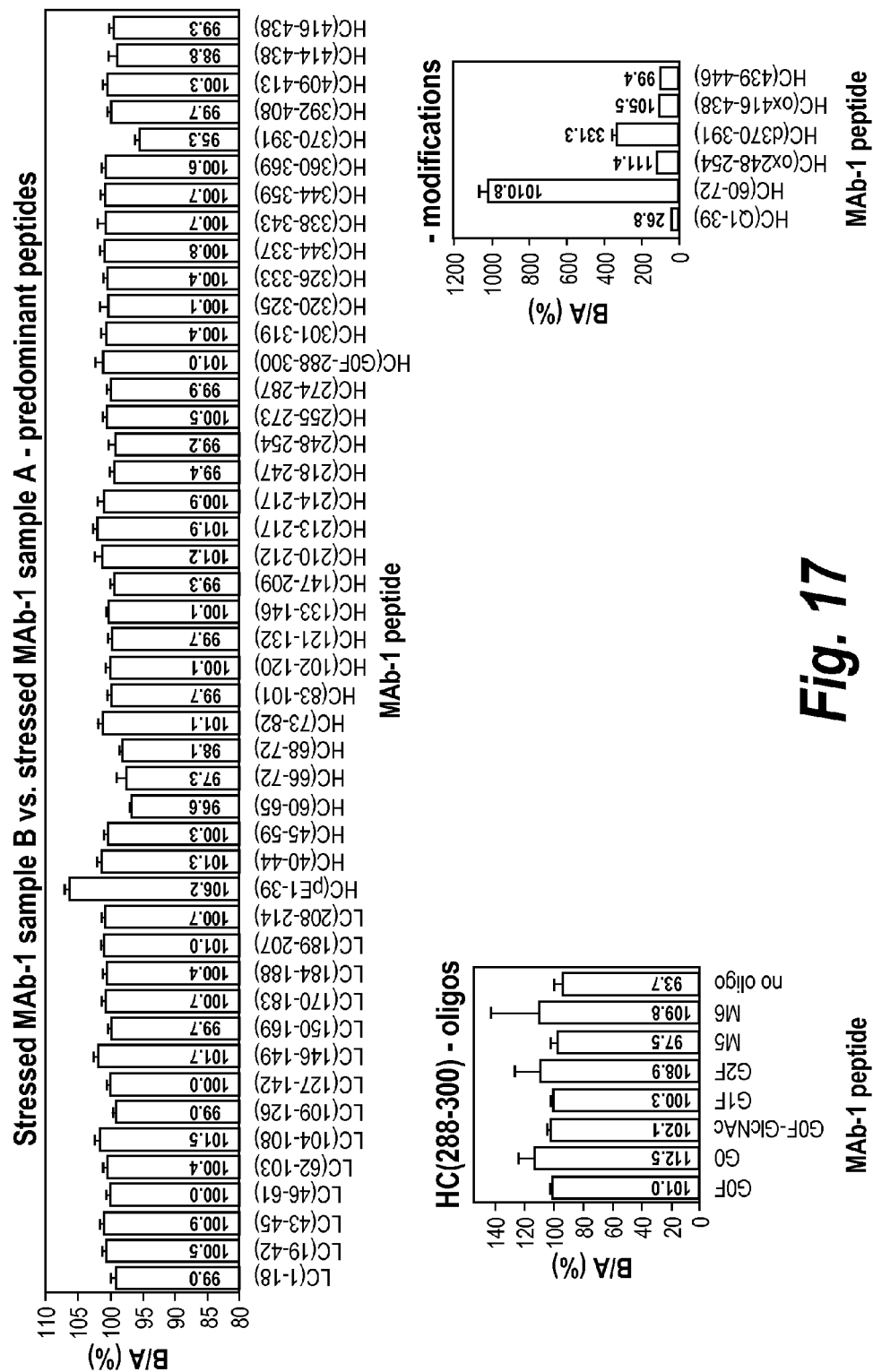
FIG. 17 is a SITRS bar graph for the comparison of mAb-1 samples mildly stressed in two different formulation buffers in accordance with the present invention.

The SITRS method was also successfully used to assess the effect of stress on an antibody. A comparison of peptides derived from a mAb stored for 6 months or 12 months at 4C in two different buffers seemed to reveal only minor differences between the two samples (FIG. 17). Nevertheless, these minor differences could be quantitated. For example, there was a 6.2% increase in the amount of pyroglutamate in HC(1-39) for the 12 month sample. This result correlated with the loss of HC(1-39) containing N-terminal Gln to 26.8% of that of the 6 month sample. In addition, HC(370-391) decreased by 4.7% This decrease was attributable to increased deamidation, as the deamidated peptide was in greater abundance in the 12 month sample by 231%. The partially digested peptide HC(60-72) (FIG. 17) was observed in the 12 month sample at 911% greater abundance over what was observed in the 6 month sample. This result correlated with a concomitant decrease in HC(60-65), HC(66-72), and HC(68-72).

Example 6

Figure 18:
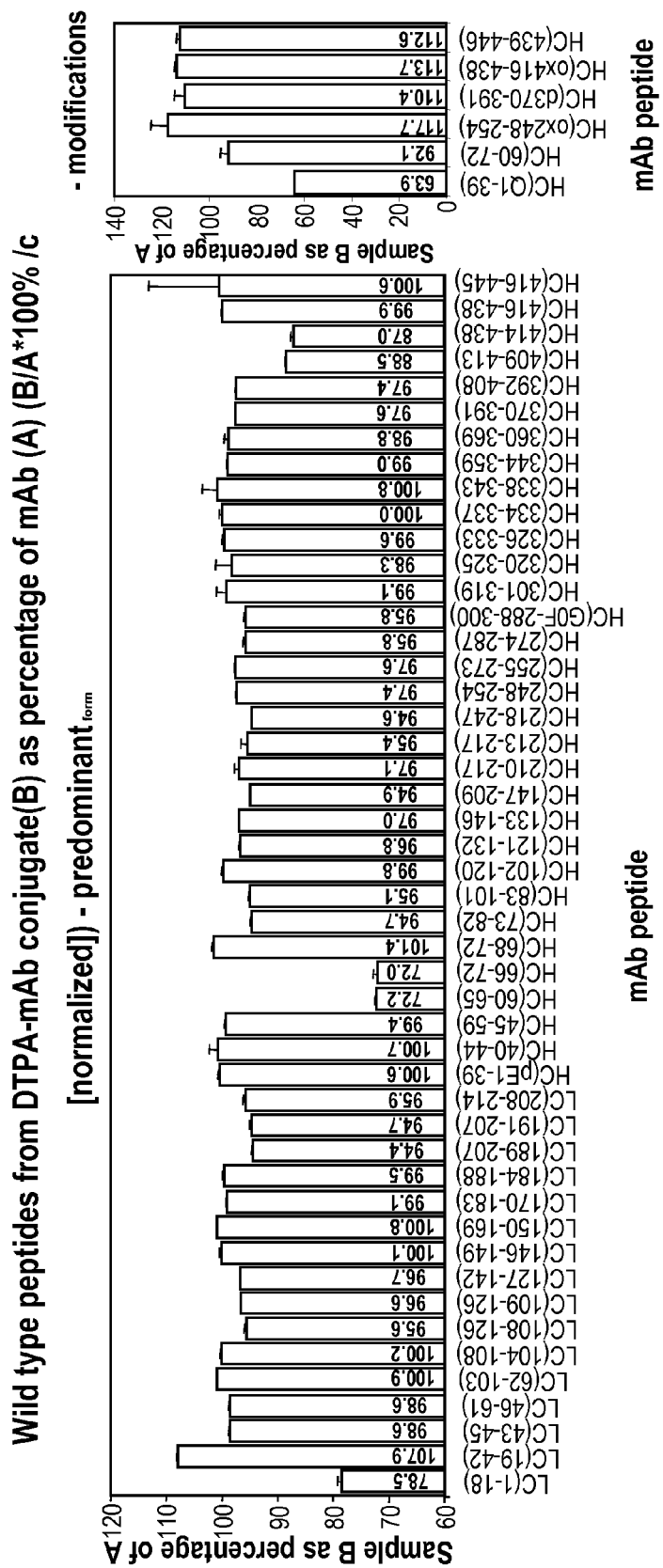
FIG. 18 is a SITRS bar graph for the comparison of DTPA-MAb-1 conjugate to unmodified MAb-1 in accordance with the present invention.

The SITRS method was also used to monitor bioconjugation experiments of small molecules, drugs or imaging agents to the protein. For example, FIG. 18 shows data from a SITRS experiment in which the metal-chelating imaging agent, CHX-A"-DTPA, was conjugated to lysine residues of the antibody. In principle, there are 92 possible reaction sites in the mAb. The SITRS experiment however, reveals that only 3 sites (peptides marked with arrows) react to an extent of >20%. These reaction sites are distinguished by the fact that the neighboring C-terminal peptide also decreases in its relative abundance by an approximately equal amount as the N-terminal peptide that was modified. This phenomenon is due to the fact that a trypsin cleavage site is lost upon conjugation with CHX-A"-DTPA.

All references cited in this specification, including without limitation, all papers, publications, patents, patent applications, presentations, texts, reports, manuscripts, brochures, books, internet postings, journal articles, and/or periodicals are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged in whole or in part. Furthermore, those of ordinary skill in the art will appreciate that the foregoing description is by way of example only, and is not intended to limit the invention so further described in such appended claims. Therefore, the spirit and scope of the appended claims should not be limited to the description of the versions contained therein.

What is claimed is:

1. A method of characterizing a protein sample, the method comprising:
   (i) providing a sample of a first protein, having a known amino acid sequence, wherein at least one amino acid in the first protein is replaced with an isotopically labeled amino acid comprising at least one heavy isotope;
   (ii) providing a sample of a second, unlabeled protein comprising an unlabeled amino acid corresponding to the isotopically labeled variant in the first protein;
   (iii) mixing the first sample and the second sample to form a mixture;
   (iv) subjecting the mixture to protein digestion to form a first digest, wherein substantially all peptides of the first protein in the digest comprise at least one isotopically labeled amino acid; subjecting the first digest to bottom-up Liquid Chromatography-Mass Spectroscopy to form a first spectra including one or more doublet or singlet peaks, each doublet peak indicating the presence of an isotopically labeled peptide from the first sample and a corresponding unlabeled peptide from the second sample and each singlet peak indicating presence of peptide with a mutation, modification, or impurity, wherein isotopically labeled peptides represented in the first spectra have a combined amino acid sequence that comprises at least 80% of the amino acid sequence of the first protein, wherein unlabeled peptides represented in the first spectra have a combined amino acid sequence that comprises at least 80% of the amino acid sequence of the second protein, and wherein the method is employed to detect a mutation, modification or impurity in the second protein sample, thereby characterizing the second protein sample.

2. The method of claim 1, further comprising the step of quantifying the amount of the unlabeled chemically distinct peptide based in a relative reduction in peak intensity.

3. The method of claim 1, wherein substantially all equivalent amino acids in the first protein are isotopically labeled.

4. The method of claim 1, wherein the protein digestion and the isotopically labeled amino acid are selected from the group consisting of:
   (a) trypsin digestion and one or more of heavy arginines, heavy lysines, and combinations thereof;
   (b) endoproteinase GluC digestion and heavy glutamic acid;
   (c) enterokinase light chain digestion and the isotopically labeled variant is selected from one or more of heavy aspartic acids, heavy lysines, and combinations thereof;
   (d) Factor Xa digestion and one or more of heavy isoleucines, heavy glutamic acids, heavy aspartic acids, heavy glycines, heavy arginines, and combinations thereof;
   (e) furin digestion and heavy arginine;
   (f) genease I digestion and one or more of heavy histidines, heavy tyrosines, and combinations thereof;
   (g) chymotrypsin digestion and a heavy aromatic amino acid;
   (h) Lys-C or Lys-N digestion and heavy lysine; and
   (i) endoproteinase ArgC digestion and heavy arginine.

5. The method of claim 1, further comprising the step of purifying the labeled protein and the unlabeled protein prior to protein digestion.

6. The method of claim 1, wherein the labeled and unlabeled proteins are individually selected from the group consisting of a recombinant protein, a biotherapeutic protein, an antibody, a monoclonal antibody, an antibody drug-conjugate, an imaging antibody, a fusion protein, and a pegylated protein.

7. The method of claim 1, wherein the labeled and unlabeled proteins are antibodies.

8. The method of claim 1, wherein the digest comprises a population of unlabeled peptides having a combined sequence representing substantially all of the complete amino acid sequence of the unlabeled protein.

9. The method of claim 8, wherein the combined sequence comprises the complete amino acid sequence of the unlabeled protein.

10. The method of claim 1, further comprising the steps of:
    (i) providing a sample of a third, unlabeled protein comprising an unlabeled amino acid corresponding to the isotopically labeled variant in the first protein;
    (ii) mixing the first sample and the third sample to form a second mixture;
    (iii) subjecting the second mixture to a second protein digestion to form a second digest; and
    (iv) subjecting the second digest to bottom-up Liquid Chromatography-Mass Spectroscopy to form a second spectra including one or more doublet or singlet peaks, each doublet peak indicating the presence of an isotopically labeled peptide from the first sample and a corresponding unlabeled peptide from the third sample and each singlet peak indicating presence of peptide with a mutation, modification, or impurity, thereby characterizing the third protein sample.

11. The method of claim 1, wherein the first protein sample is an innovator biologic and the second protein sample is a biosimilar of the innovator biologic.

12. The method of claim 1, wherein the first protein sample is an unconjugated protein and the second protein sample is a conjugated protein.

13. The method of claim 1, wherein the first and second protein samples are produced in different cell lines, different cell types or different manufacturing processes.

14. The method of claim 1, wherein the first and second protein samples have been stored under different storage conditions.

15. The method of claim 1, wherein the mutation, modification or impurity is selected from the group consisting of altered oligosaccharide content, a N-terminal glutamine conversion, C-terminal lysine removal, altered pyroglutamate content, and increased deamidation or oxidation.

16. The method of claim 1, wherein the first and second samples are substantially homogenous protein preparations.

17. The method of claim 1, wherein the first and second samples are pharmaceutical compositions.

* * * * *